(12) United States Patent
Getman et al.

(10) Patent No.: US 10,597,738 B2
(45) Date of Patent: *Mar. 24, 2020

(54) COMPOSITIONS, METHODS AND KITS TO DETECT HERPES SIMPLEX VIRUS NUCLEIC ACID

(71) Applicant: GEN-PROBE INCORPORATED, San Diego, CA (US)

(72) Inventors: Damon K. Getman, Poway, CA (US); Aparna Aiyer, San Diego, CA (US); Wendy Chen, Diamond Bar, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 130 days.

This patent is subject to a terminal disclaimer.

(21) Appl. No.: 15/968,292

(22) Filed: May 1, 2018

(65) Prior Publication Data

US 2018/0355444 A1 Dec. 13, 2018

Related U.S. Application Data

(63) Continuation of application No. 14/944,532, filed on Nov. 18, 2015, now Pat. No. 9,994,921, which is a continuation of application No. 13/642,428, filed as application No. PCT/US2011/033488 on Apr. 21, 2011, now Pat. No. 9,206,484.

(60) Provisional application No. 61/326,329, filed on Apr. 21, 2010.

(51) Int. Cl.
*C12Q 1/68* (2018.01)
*C12Q 1/70* (2006.01)
*C12Q 1/6865* (2018.01)

(52) U.S. Cl.
CPC .......... *C12Q 1/705* (2013.01); *C12Q 1/6865* (2013.01); *C12Q 2600/158* (2013.01)

(58) Field of Classification Search
None
See application file for complete search history.

(56) References Cited

U.S. PATENT DOCUMENTS

| 2005/0112561 A1 | 5/2005 | Walkerpeach et al. |
| 2006/0088865 A1 | 4/2006 | Adelson et al. |
| 2007/0141559 A1 | 6/2007 | Exner |

(Continued)

FOREIGN PATENT DOCUMENTS

| EP | 2098599 A1 | 9/2009 |
| EP | 2262908 | 9/2009 |

(Continued)

OTHER PUBLICATIONS

Georgopoulou et al., Characterization of the US8.5 protein of herpes simplex virus, Arch Virol. 1995;140(12):2227-41.*

(Continued)

*Primary Examiner* — Aaron A Priest
(74) *Attorney, Agent, or Firm* — Jeff Landes; Alston & Bird LLP

(57) ABSTRACT

The disclosed invention is related to methods, compositions, kits and isolated nucleic acid sequences for targeting Herpes Simplex Virus (HSV) nucleic acid (eg. HSV-1 and/or HSV-2 nucleic acid). Compositions include amplification oligomers, detection probe oligomers and/or target capture oligomers. Kits and methods comprise at least one of these oligomers.

10 Claims, 8 Drawing Sheets

Specification includes a Sequence Listing.

(56) References Cited

U.S. PATENT DOCUMENTS

| | | |
|---|---|---|
| 2007/0202523 A1 | 8/2007 | Becker et al. |
| 2011/0091885 A1 | 4/2011 | Schmitt et al. |

FOREIGN PATENT DOCUMENTS

| | | | | |
|---|---|---|---|---|
| WO | WO 2001/76643 A1 | 10/2001 | | |
| WO | WO-0176643 A1 * | 10/2001 | ............ | A61K 39/21 |
| WO | WO 2002/061390 A2 | 8/2002 | | |
| WO | WO 2004/097029 A2 | 11/2004 | | |
| WO | WO 2005/080581 A2 | 9/2005 | | |
| WO | WO-2005080581 A2 * | 9/2005 | ............ | C12N 15/85 |
| WO | WO 2006/053779 A2 | 5/2006 | | |
| WO | WO 2008/055691 A1 | 5/2008 | | |
| WO | WO 2009/109611 A1 | 9/2009 | | |
| WO | WO 2009/122201 A1 | 10/2009 | | |
| WO | WO 2011/133811 A2 | 10/2011 | | |

OTHER PUBLICATIONS

Georgopoulou et al., Identification of a New Transcriptional Unit That Yields a Gene Product within the Unique Sequences of the Short Component of the Herpes Simplex Virus 1 Genome, J Virol. Jul. 1993;67(7):3961-8.*

Sciortino et al., RNAs Extracted from Herpes Simplex Virus 1 Virions: Apparent Selectivity of Viral but Not Cellular RNAs Packaged in Virions, J Virol. Sep. 2001;75(17):8105-16.*

Bresnahan et al. "A Subset of Viral Trancripts Packaged Within Human Cytomegatovirus Particles." Science, Jun. 30, 2000, pp. 2373-2376, vol. 288, www.sciencemag.org>.

CIPO Office Action, Canadian Patent Application No. 2,796,457, dated Dec. 7, 2015.

Deiman et al. "Efficient amplification with BASBA® of hepatitis B virus, herpes simplex virus and methicillin resistant *Staphylococcus aureus* DNA." J. of Virological Methods, Aug. 1, 2008, pp. 283-293, vol. 151, No. 2, Elsevier Science Ltd., Amsterdam, Netherlands.

Dolan et al. "The Genome Sequence of Herpes Simplex Virus Type 2." J. of Virol., Mar. 1998, pp. 2010-2021, vol. 72, No. 3, Am. Society for Microbiology, Washington D.C., USA.

Emery et al., "Evaluation of Performance of the Gen-Probe Human Immunodeficiency Virus Type 1 Viral Load Assay Using Primary Subtype A, C, and D Isolates from Kenya," J. Clin. Microbiol., 2000 38(7):2688-2695, Am. Society for Microbiology, Washington D.C.

EPO Communication Pursuant to Article 94(3) EPC, European Application No. 16155979.4, dated Mar. 26, 2018.

EPO Communication Pursuant to Article 94(3) EPC, European Patent Application No. 16155979.4, dated Sep. 6, 2017.

EPO Extended European Search Report, European Patent Application No. 16155979.4, dated May 11, 2016.

European Patent Office Examination Report, Application No. 11718828.4, dated May 8, 2014.

Georgopoulou et al., Characterization of the US8.5 protein of herpes simplex virus, Arch Virol. 1995; 140(12):2227-14.

Georgopoulou et al. "Identification of a New Transcriptional Unit That Yields a Gene Product within the Unique Sequences of the Short Component of the Herpes Simplex Virus 1 Genome." J. of Virol., Jul. 1993, pp. 3961-3968, vol. 67, No. 7, Am. Society for Microbiology.

Georgopoulou et al. "Characterization of the US8.5 protein of herpes simplex virus." Arch. Virol., 1995, pp. 2227-2241, vol. 140, Springer-Verlag, Austria.

Gottlieb et al., "The Herpes Simplex Virus Type 1 UL42 Gene Product: a Subunit of DNA Polymerase That Functions to Increase Processivity." J. of Virol., Dec. 1990, pp. 5976-5987, vol. 64, No. 12, Am. Society for Microbiology, Washington D.C., USA.

Greijer et al., "Human Cytomegalovirus Virions Differentially Incorporate Viral and Host Cell RNA during the Assembly Process." J. of Virol., Oct. 2000, pp. 9078-9082, vol. 74, No. 19, Am. Society for Microbiology, Washington D.C., USA.

Greijer et al., "Multiplex real-time NASBA for monitoring expression dynamics of human cytomegalovirus encoded IE1 and pp67 RNA." J. of Clin. Virol., 2002, pp. 57-66, vol. 24, Elsevier Science Ltd., Amsterdam, NL.

International Preliminary Report on Patentability, International Application No. PCT/US2011/033488, dated Oct. 23, 2012.

International Search Report, International Application No. PCT/US2011/033488, dated Jan. 6, 2012.

McGeoh et al., "The Complete DNA Sequence of the Long Unique Region in the Genome of Herpes Simplex Virus Type 1." J. Gen. Virol., 1988, pp. 1531-1574, vol. 69, Great Britain.

Primer3Plus: pick primers from a DNA sequence, http://www.bioinformatics.nl/chi-bin/primer3plus/primer3plus.cgi, (Accessed on Feb. 5, 2015).

Rixon et al., "Detailed analysis of the miRNAs mapping in the short unique region of herpes simplex virus type 1." Nucleic Acids Research, 1985, pp. 953-973, vol. 13, No. 3, IRL Press Limited, Oxford, England.

Rozen et al., "Primer3 on the WWW for General Users and for Biologist Programmers," Methods in Molecular Biology, 2000, vol. 132(20):Bioinformatics Methods and Protocols, pp. 365-386, Humana Press Inc., New Jersey, USA.

Sarcinella et al., "Detection of RNA in purified cytomegalovirus virions." Virus Research, 2004, pp. 129-137, vol. 104, Elsevier Science Ltd., Amsterdam, NL.

Sauerbrei et al., "Virological diagnosis of herpes simplex encephalitis." J. of Clin. Virol., 2000, pp. 31-36, vol. 17, Elsevier Science Ltd., Amsterdam, NL.

Sciortino et al., "Of the three tegument proteins that package mRNA in herpes simplex virions, one (VP22) transports the mRNA to uninfected cells for expression prior to viral infection." Proc Natl Acad Sci USA., Jun. 11, 2002, pp. 8318-8323, vol. 99, N.

Sciortino et al., "RNAs Extracted from Herpes Simplex Virus 1 Virions: Apparent Selectivity of Viral but Not Cellular RNAs Packaged in Virions." J. of Virol., Sep. 1, 2001, pp. 8105-8116, vol. 75, No. 17, Am. Society for Microbiology, Washington D.C.

Sciortino, BLAST®, Basic Local Alignment Search Tool, NCBI Blast: Nucleotide Sequence (470 letters), RID: D7Y0EJUX114, http://blast.ncbi.nlm.nih.gov/Blast.cgi, (Accessed on Feb. 5, 2015).

Terhune et al. "RNAs Are Packaged into Human Cytomegalovirus Virions in Proportion to Their Intracellular Concentration." J. of Virol., Oct. 2004, pp. 10390-10398, vol. 78, No. 19, Am. Society for Microbiology, Washington D.C., USA.

U.S. Appl. No. 13/642,428, Non-Final Office Action dated Mar. 2, 2015.

U.S. Appl. No. 13/642,428, Notice of Allowance dated Aug. 5, 2015.

U.S. Appl. No. 13/642,428, Notice of Allowance dated Aug. 14, 2015.

U.S. Appl. No. 13/642,428, Requirement for Restriction/Election dated Oct. 8, 2014.

U.S. Appl. No. 14/944,532, Notice of Allowance dated Apr. 19, 2018.

U.S. Appl. No. 14/944,532, Requirement for Restriction/Election dated Aug. 16, 2017.

Untergasser et al., "Primer3Plus, an enhanced web interface to Primer3," Nucleic Acids Res., 2007, 35:W71-W74, Web-Server Issue, Oxford University Press, UK.

Written Opinion, International Application No. PCT/US2011/033488, dated Jan. 6, 2012.

Xing et al. "Packaging of viral RNAs in virions of adenoviruses." Virology Journal, Feb. 5, 2009, vol. 6, No. 16, BioMed Central Ltd.

Zuccola et al. "The Crystal Structure of an Unusual Processivity Factor, Herpes Simplex Virus UL42, Bound to the C Terminus of Its Cognate Polymerase." Molecular Cell, Feb. 2000, pp. 267-278, vol. 5, No. 2, Cell Press.

* cited by examiner

```
                10         20         30         40         50         60         70
             ....|....|....|....|....|....|....|....|....|....|....|....|....|....|
US8 gene     CATTTAAGGCGTTGTTGTGTTGACTTTGCCTCTTCTGGCGGGTTGGTGCGGTGCTGTTTGTTGGGCTCCC
US8.5 (US8A) ----------------------------------------------------------------------

80         90        100        110        120        130        140
             ....|....|....|....|....|....|....|....|....|....|....|....|....|....|
US8 gene     ATTTTACCCGAAGATCGGCTGCTATCCCCGGGACATGGATCGCGGGGCGGTGGTGGGGTTTCTTCTCGGT
US8.5 (US8A) ----------------------------------------------------------------------

150        160        170        180        190        200        210
             ....|....|....|....|....|....|....|....|....|....|....|....|....|....|
US8 gene     GTTTGTGTTGTATCGTGCTTGGCGGGAACGCCCAAAACGTCCTGGAGACGGGTGAGTGTCGGCGAGGACG
US8.5 (US8A) ----------------------------------------------------------------------

220        230        240        250        260        270        280
             ....|....|....|....|....|....|....|....|....|....|....|....|....|....|
US8 gene     TTTCGTTGCTTCCAGCTCCGGGGCCTACGGGGCGCGGCCCGACCCAGAAACTACTATGGGCCGTGGAACC
US8.5 (US8A) ----------------------------------------------------------------------

290        300        310        320        330        340        350
             ....|....|....|....|....|....|....|....|....|....|....|....|....|....|
US8 gene     CCTGGATGGGTGCGGCCCCTTACACCCGTCGTGGGTCTCGCTGATGCCCCCCAAGCAGGTGCCCGAGACG
US8.5 (US8A) ----------------------------------------------------------------------

360        370        380        390        400        410        420
             ....|....|....|....|....|....|....|....|....|....|....|....|....|....|
US8 gene     GTCGTGGATGCGGCGTGCATGCGCGCTCCGGTCCCGCTGGCGATGGCGTACGCCCCCCGGCCCCATCTG
US8.5 (US8A) ----------------------------------------------------------------------

430        440        450        460        470        480        490
             ....|....|....|....|....|....|....|....|....|....|....|....|....|....|
US8 gene     CGACCGGGGGTCTACGAACGGACTTCGTGTGGCAGGAGCGCGCGGCCGTGGTTAACCGGAGTCTGGTTAT
US8.5 (US8A) ----------------------------------------------------------------------

500        510        520        530        540        550        560
             ....|....|....|....|....|....|....|....|....|....|....|....|....|....|
US8 gene     TCACGGGGTCCGAGAGACGGACAGCGGCCTGTATACCCTGTCCGTGGGCGACATAAAGGACCCGGCTCGC
US8.5 (US8A) ----------------------------------------------------------------------

570        580        590        600        610        620        630
             ....|....|....|....|....|....|....|....|....|....|....|....|....|....|
US8 gene     CAAGTGGCCTCGGTGGTCCTGGTGGTGCAACCGGCCCCAGTTCCGACCCCACCCCCGACCCCAGCCGATT
US8.5 (US8A) ----------------------------------------------------------------------

640        650        660        670        680        690        700
             ....|....|....|....|....|....|....|....|....|....|....|....|....|....|
US8 gene     ACGACGAGGATGACAATGACGAGGGCGAGGACGAAAGTCTCGCCGGCACTCCCGCCAGCGGGACCCCCCG
US8.5 (US8A) ----------------------------------------------------------------------

710        720        730        740        750        760        770
             ....|....|....|....|....|....|....|....|....|....|....|....|....|....|
US8 gene     GCTCCCGCCTCCCCCCGCCCCCCCGAGGTCTTGGCCCAGCGCCCCCGAAGTCTCACATGTGCGTGGGGTG
US8.5 (US8A) ----------------------------------------------------------------------
```

FIGURE 1

```
                   780        790        800        810        820        830        840
               ....|....|....|....|....|....|....|....|....|....|....|....|....|....|
US8 gene       ACCGTGCGTATGGAGACTCCGGAAGCTATCCTGTTTTCCCCCGGGGAGACGTTCAGCACGAACGTCTCCA
US8.5 (US8A)   ----------------------------------------------------------------------

850        860        870        880        890        900        910
               ....|....|....|....|....|....|....|....|....|....|....|....|....|....|
US8 gene       TCCATGCCATCGCCCACGACGACCAGACCTACTCCATGGACGTCGTCTGGTTGAGGTTCGACGTGCCGAC
US8.5 (US8A)   ----------------------------------------------------------------------

920        930        940        950        960        970        980
               ....|....|....|....|....|....|....|....|....|....|....|....|....|....|
US8 gene       CTCGTGTGCCGAGATGCGAATATACGAATCGTGTCTGTATCACCCGCAGCTCCCAGAATGTCTGTCCCCG
US8.5 (US8A)   ----------------------------------------------------------------------

990       1000       1010       1020       1030       1040       1050
               ....|....|....|....|....|....|....|....|....|....|....|....|....|....|
US8 gene       GCCGACGCGCCGTGCGCCGCGAGTACGTGGACGTCTCGCCTGGCCGTCCGCAGCTACGCGGGGTGTTCCA
US8.5 (US8A)   ----------------------------------------------------------------------

1060       1070       1080       1090       1100       1110       1120
               ....|....|....|....|....|....|....|....|....|....|....|....|....|....|
US8 gene       GAACAAACCCCCCACCGCGCTGTTCGGCCGAGGCTCACATGGAGCCCGTCCCGGGGCTGGCGTGGCAGGC
US8.5 (US8A)   ----------------------------------------------------------------------

1130       1140       1150       1160       1170       1180       1190
               ....|....|....|....|....|....|....|....|....|....|....|....|....|....|
US8 gene       GGCCTCCGTCAATCTGGAGTTCCGGGACGCGTCCCCACAACACTCCGGCCTGTATCTGTGTGGTGTAC
US8.5 (US8A)   ----------------------------------------------------------------------

1200       1210       1220       1230       1240       1250       1260
               ....|....|....|....|....|....|....|....|....|....|....|....|....|....|
US8 gene       GTCAACGACCATATTCACGCCTGGGGCCACATTACCATCAGCACCGCGGCGCAGTACCGGAACGCGGTGG
US8.5 (US8A)   ----------------------------------------------------------------------

1270       1280       1290       1300       1310       1320       1330
               ....|....|....|....|....|....|....|....|....|....|....|....|....|....|
US8 gene       TGGAACAGCCCCTCCCACAGCGCGGCGCGGATTTGGCCGAGCCCACCCACCCGCACGTCGGGGCCCCTCC
US8.5 (US8A)   ----------------------------------------------------------------------

1340       1350       1360       1370       1380       1390       1400
               ....|....|....|....|....|....|....|....|....|....|....|....|....|....|
US8 gene       CCACGCGCCCCCAACCCACGGCGCCCTGCGGTTAGGGGCGGTGATGGGGGCCGCCCTGCTGCTGTCTGCA
US8.5 (US8A)   ----------------------------------------------------------------------

1410       1420       1430       1440       1450       1460       1470
               ....|....|....|....|....|....|....|....|....|....|....|....|....|....|
US8 gene       CTGGGGTTGTCGGTGTGGGCGTGTATGACCTGTTGGCGCAGGCGTGCCTGGCGGGCGGTTAAAAGCAGGG
US8.5 (US8A)   ----------------------------------------------------------------------

1480       1490       1500       1510       1520       1530       1540
               ....|....|....|....|....|....|....|....|....|....|....|....|....|....|
US8 gene       CCTCGGGTAAGGGGCCCACGTACATTCGCGTGGCCGACAGCGAGCTGTACGCGGACTGGAGCTCGGACAG
US8.5 (US8A)   ----------------------------------------------------------------------
```

FIGURE 1 (continued)

```
                       1550       1560       1570       1580       1590       1600       1610
                  ....|....|....|....|....|....|....|....|....|....|....|....|....|....|
US8 gene          CGAGGGAGAACGCGACCAGGTCCCGTGGCTGGCCCCCCCGGAGAGACCCGACTCTCCCTCCACCAATGGA
US8.5 (US8A)      ----------------------------------------------------------------ATGGA 1620       1630       1640       1650       1660       1670       1680
                  ....|....|....|....|....|....|....|....|....|....|....|....|....|....|
US8 gene          TCCGGCTTTGAGATCTTATCACCAACGGCTCCGTCTGTATACCCCCGTAGCGATGGGCATCAATCTCGCC
US8.5 (US8A)      TCCGGCTTTGAGATCTTATCACCAACGGCTCCGTCTGTATACCCCCGTAGCGATGGGCATCAATCTCGCC 1690       1700       1710       1720       1730       1740       1750
                  ....|....|....|....|....|....|....|....|....|....|....|....|....|....|
US8 gene          GCCAGCTCACAACCTTTGGATCCGGAAGGCCCGATCGCCGTTACTCCCAGGCCTCCGATTCGTCCGTCTT
US8.5 (US8A)      GCCAGCTCACAACCTTTGGATCCGGAAGGCCCGATCGCCGTTACTCCCAGGCCTCCGATTCGTCCGTCTT 1760       1770       1780       1790       1800       1810       1820
                  ....|....|....|....|....|....|....|....|....|....|....|....|....|....|
US8 gene          CTGGTAAGGCGCCCCATCCCGAGGCCCCACGTCGGTCGCCGAACTGGGCGACCGCCGGCGAGGTGGACGT
US8.5 (US8A)      CTGGTAAGGCGCCCCATCCCGAGGCCCCACGTCGGTCGCCGAACTGGGCGACCGCCGGCGAGGTGGACGT 1830       1840       1850       1860       1870       1880       1890
                  ....|....|....|....|....|....|....|....|....|....|....|....|....|....|
US8 gene          CGGAGACGAGCTAATCGCGATTTCCGACGAACGCGGACCCCCCCGACATGACCGCCCGCCCCTCGCCACG
US8.5 (US8A)      CGGAGACGAGCTAATCGCGATTTCCGACGAACGCGGACCCCCCCGACATGACCGCCCGCCCCTCGCCACG 1900       1910       1920       1930       1940       1950       1960
                  ....|....|....|....|....|....|....|....|....|....|....|....|....|....|
US8 gene          TCGACCGCGCCCTCGCCACACCCGCGACCCCCGGGCTACACGGCCGTTGTCTCCCCGATGGCCCTCCAGG
US8.5 (US8A)      TCGACCGCGCCCTCGCCACACCCGCGACCCCCGGGCTACACGGCCGTTGTCTCCCCGATGGCCCTCCAGG 1970       1980       1990       2000       2010       2020       2030
                  ....|....|....|....|....|....|....|....|....|....|....|....|....|....|
US8 gene          CTGTCGACGCCCCCTCCCTGTTTGTCGCCTGGCTGGCCGCTCGGTGGCTCCGGGGGCTTCCGGCCTGGG
US8.5 (US8A)      CTGTCGACGCCCCCTCCCTGTTTGTCGCCTGGCTGGCCGCTCGGTGGCTCCGGGGGCTTCCGGCCTGGG 2040       2050       2060       2070       2080       2090       2100
                  ....|....|....|....|....|....|....|....|....|....|....|....|....|....|
US8 gene          GGCCGTCCTGTGTGGGATTGCGTGGTATGTGACGTCAATTGCCCGAGGCGCATAAAGGGCCGGTGGTCCG
US8.5 (US8A)      GGCCGTCCTGTGTGGGATTGCGTGGTATGTGACGTCAATTGCCCGAGGCGCATAAAGGGCCGGTGGTCCG 2110       2120       2130       2140       2150       2160       2170
                  ....|....|....|....|....|....|....|....|....|....|....|....|....|....|
US8 gene          CCTAGCCGCAGCAAATTAAAAATCGTGAGTCACAGCGACCGCAACTTCCCACCCGGAGCTTTCTTCCGGC
US8.5 (US8A)      CCTAGCCGCAGCAAATTAAAAATCGTGAGTCACAGCGACCGCAACTTCCCACCCGGAGCTTTCTTCCGGC 2180       2190       2200       2210       2220       2230       2240
                  ....|....|....|....|....|....|....|....|....|....|....|....|....|....|
US8 gene          CTCGATGACGTCCCGGCTCTCCGATCCCAACTCCTCAGCGCGATCCGACATGTCCGTGCCGCTTTATCCC
US8.5 (US8A)      CTCGATGACGTCCCGGCTCTCCGATCCCAACTCCTCAGCGCGATCCGACATGTCCGTGCCGCTTTATCCC
```

FIGURE 1 (continued)

```
                    2250       2260       2270       2280       2290       2300       2310
                ....|....|....|....|....|....|....|....|....|....|....|....|....|....|
US8 gene        ACGGCCTCGCCAGTTTCGGTCGAAGCCTACTACTCGGAAAGCGAAGACGAGGCGGCCAACGACTTCCTCG
US8.5 (US8A)    ACGGCCTCGCCAGTTTCGGTCGAAGCCTACTACTCGGAAAGCGAAGACGAGGCGGCCAACGACTTCCTCG 2320       2330       2340       2350       2360       2370       2380
                ....|....|....|....|....|....|....|....|....|....|....|....|....|....|
US8 gene        TACGCATGGGCCGCCAACAGTCGGTATTAAGGCGTCGACGCAGACGCACCCGCTGCGTCGGCATGGTGAT
US8.5 (US8A)    TACGCATGGGCCGCCAACAGTCGGTATTAAGGCGTCGACGCAGACGCACCCGCTGCGTCGGCATGGTGAT 2390       2400       2410       2420       2430       2440       2450
                ....|....|....|....|....|....|....|....|....|....|....|....|....|....|
US8 gene        CGCCTGTCTCCTCGTGGCCGTTCTGTCGGGCGGATTTGGGGCGCTCCTGATGTGGCTGCTCCGCTAAAAG
US8.5 (US8A)    CGCCTGTCTCCTCGTGGCCGTTCTGTCGGGCGGATTTGGGGCGCTCCTGATGTGGCTGCTCCGCTAAAAG 2460       2470       2480       2490       2500       2510       2520
                ....|....|....|....|....|....|....|....|....|....|....|....|....|....|
US8 gene        ACCGCATCGACACGCGCGTCCTTCTTGTCGTCTCTCTTCCCCCCCATCACCCCGCAATTTGCACCCAGCC
US8.5 (US8A)    ACCGCATCGACACGCGCGTCCTTCTTGTCGTCTCTCTTCCCCCCCATCACCCCGCAATTTGCACCCAGCC 2530       2540       2550
                ....|....|....|....|....|....|
US8 gene        TTTAACTACATTAAATTGGGTTCGATTGGCAATGT
US8.5 (US8A)    TTTAACTACATTAAATTGGGTTCGATTGGCAATGT
```

FIGURE 1 (continued)

```
                        10         20         30         40         50         60         70
                  ....|....|....|....|....|....|....|....|....|....|....|....|....|....|
US8 gene          ATGGCTCGCGGGGCCGGGTTGGTGTTTTTTGTTGGAGTTTGGGTCGTATCGTGCCTGGCGGCAGCACCCA
US8.5 (US8A)      ----------------------------------------------------------------------

80         90        100        110        120        130        140
                  ....|....|....|....|....|....|....|....|....|....|....|....|....|....|
US8 gene          GAACGTCCTGGAAACGGGTAACCTCGGGCGAGGACGTGGTGTTGCTTCCGGCGCCCGCGGAACGCACCCG
US8.5 (US8A)      ----------------------------------------------------------------------

150        160        170        180        190        200        210
                  ....|....|....|....|....|....|....|....|....|....|....|....|....|....|
US8 gene          GGCCCACAAACTACTGTGGGCCGCGGAACCCCTGGATGCCTGCGGTCCCCTGCGCCCGTCGTGGGTGGCG
US8.5 (US8A)      ----------------------------------------------------------------------

220        230        240        250        260        270        280
                  ....|....|....|....|....|....|....|....|....|....|....|....|....|....|
US8 gene          CTGTGGCCCCCCCGACGGGTGCTCGAGACGGTCGTGGATGCGGCGTGCATGCGCGCCCCGGAACCGCTCG
US8.5 (US8A)      ----------------------------------------------------------------------

290        300        310        320        330        340        350
                  ....|....|....|....|....|....|....|....|....|....|....|....|....|....|
US8 gene          CCATAGCATACAGTCCCCCGTTCCCCGCGGGCGACGAGGGACTGTATTCGGAGTTGGCGTGGCGCGATCG
US8.5 (US8A)      ----------------------------------------------------------------------

360        370        380        390        400        410        420
                  ....|....|....|....|....|....|....|....|....|....|....|....|....|....|
US8 gene          CGTAGCCGTGGTCAACGAGAGTCTGGTCATCTACGGGGCCCTGGAGACGGACAGCGGTCTGTACACCCTG
US8.5 (US8A)      ----------------------------------------------------------------------

430        440        450        460        470        480        490
                  ....|....|....|....|....|....|....|....|....|....|....|....|....|....|
US8 gene          TCCGTGGTCGGCCTAAGCGACGAGGCGCGCCAAGTGGCGTCGGTGGTTCTGGTCGTGGAGCCCGCCCCTG
US8.5 (US8A)      ----------------------------------------------------------------------

500        510        520        530        540        550        560
                  ....|....|....|....|....|....|....|....|....|....|....|....|....|....|
US8 gene          TGCCGACCCCGACCCCCGACGACTACGACGAAGAAGACGACGCGGGCGTGACGAACGCACGCCGGTCAGC
US8.5 (US8A)      ----------------------------------------------------------------------

570        580        590        600        610        620        630
                  ....|....|....|....|....|....|....|....|....|....|....|....|....|....|
US8 gene          GTTCCCCCCCAACCCCCCCCCCGTCGTCCCCCCGTCGCCCCCCCGACGCACCCTCGTGTTATCCCCGAG
US8.5 (US8A)      ----------------------------------------------------------------------

640        650        660        670        680        690        700
                  ....|....|....|....|....|....|....|....|....|....|....|....|....|....|
US8 gene          GTGTCCCACGTGCGCGGGGTAACGGTCCATATGGAGACCCTGGAGGCCATTCTGTTTGCCCCCGGGGAGA
US8.5 (US8A)      ----------------------------------------------------------------------

710        720        730        740        750        760        770
                  ....|....|....|....|....|....|....|....|....|....|....|....|....|....|
US8 gene          CGTTTGGGACGAACGTCTCCATCCACGCCATTGCCCACGACGACGGTCCGTACGCCATGGACGTCGTCTG
US8.5 (US8A)      ----------------------------------------------------------------------
```

FIGURE 2

```
                    780       790       800       810       820       830       840
                    ....|....|....|....|....|....|....|....|....|....|....|....|....|....|
US8 gene            GATGCGGTTTGACGTGCCGTCCTCGTGCGCCGATATGCGGATCTACGAAGCTTGTCTGTATCACCCGCAG
US8.5 (US8A)        ----------------------------------------------------------------------

850       860       870       880       890       900       910
                    ....|....|....|....|....|....|....|....|....|....|....|....|....|....|
US8 gene            CTTCCAGAGTGTCTATCTCCGGCCGACGCGCCGTGCGCCGTAAGTTCCTGGGCGTACCGCCTGGCGGTCC
US8.5 (US8A)        ----------------------------------------------------------------------

920       930       940       950       960       970       980
                    ....|....|....|....|....|....|....|....|....|....|....|....|....|....|
US8 gene            GCAGCTACGCCGGCTGTTCCAGGACTACGCCCCCGCCGCGATGTTTTGCCGAGGCTCGCATGGAACCGGT
US8.5 (US8A)        ----------------------------------------------------------------------

990       1000      1010      1020      1030      1040      1050
                    ....|....|....|....|....|....|....|....|....|....|....|....|....|....|
US8 gene            CCCGGGGTTGGCGTGGCTGGCCTCCACCGTCAATCTGGAATTCCAGCACGCCTCCCCCCAGCACGCCGGC
US8.5 (US8A)        ----------------------------------------------------------------------

1060      1070      1080      1090      1100      1110      1120
                    ....|....|....|....|....|....|....|....|....|....|....|....|....|....|
US8 gene            CTCTACCTGTGCGTGGTGTACGTGGACGATCATATCCACGCCTGGGGCCACATGACCATCAGCACCGCGG
US8.5 (US8A)        ----------------------------------------------------------------------

1130      1140      1150      1160      1170      1180      1190
                    ....|....|....|....|....|....|....|....|....|....|....|....|....|....|
US8 gene            CGCAGTACCGGAACGCGGTGGTGGAACAGCACCTCCCCCAGCGCCAGCCCGAGCCCGTCGAGCCCACCCG
US8.5 (US8A)        ----------------------------------------------------------------------

1200      1210      1220      1230      1240      1250      1260
                    ....|....|....|....|....|....|....|....|....|....|....|....|....|....|
US8 gene            CCCGCACGTGAGAGCCCCCCATCCCGCGCCCTCCGCGCGCGGCCCGCTGCGCCTCGGGGCGGTGCTGGGG
US8.5 (US8A)        ----------------------------------------------------------------------

1270      1280      1290      1300      1310      1320      1330
                    ....|....|....|....|....|....|....|....|....|....|....|....|....|....|
US8 gene            GCGGCCCTGTTGCTGGCCGCCCTCGGGCTGTCCGCGTGGGCGTGCATGACCTGCTGGCGCAGGCGCTCCT
US8.5 (US8A)        ----------------------------------------------------------------------

1340      1350      1360      1370      1380      1390      1400
                    ....|....|....|....|....|....|....|....|....|....|....|....|....|....|
US8 gene            GGCGGGCGGTTAAAAGCCGGGCCTCGGCGACGGGCCCCACTTACATTCGCGTGGCGGACAGCGAGCTGTA
US8.5 (US8A)        ----------------------------------------------------------------------

1410      1420      1430      1440      1450      1460      1470
                    ....|....|....|....|....|....|....|....|....|....|....|....|....|....|
US8 gene            CGCGGACTGGAGTTCGGACAGCGAGGGGGAGCGCGACGGGTCCCTGTGGCAGGACCCTCCGGAGAGACCC
US8.5 (US8A)        ----------------------------------------------------------------------
```

FIGURE 2 (continued)

```
                    1480       1490       1500       1510       1520       1530       1540
                ....|....|....|....|....|....|....|....|....|....|....|....|....|....|
US8 gene        GACTCTCCCTCCACAAATGGATCCGGCTTTGAGATCTTATCACCAACGGCTCCGTCTGTATACCCCCATA
US8.5 (US8A)    ----------------ATGGATCCGGCTTTGAGATCTTATCACCAACGGCTCCGTCTGTATACCCCCATA 1550       1560       1570       1580       1590       1600       1610
                ....|....|....|....|....|....|....|....|....|....|....|....|....|....|
US8 gene        GCGAGGGGCGTAAATCTCGCCGCCCGCTCACCACCTTTGGTTCGGGAAGCCCGGGCCGTCGTCACTCCCA
US8.5 (US8A)    GCGAGGGGCGTAAATCTCGCCGCCCGCTCACCACCTTTGGTTCGGGAAGCCCGGGCCGTCGTCACTCCCA 1620       1630       1640       1650       1660       1670       1680
                ....|....|....|....|....|....|....|....|....|....|....|....|....|....|
US8 gene        GGCCTCCTATCCGTCCGTCCTCTGGTAAGGCGTCTTCCGACGACGCGGACGTCGGCGATGAACTGATTGC
US8.5 (US8A)    GGCCTCCTATCCGTCCGTCCTCTGGTAAGGCGTCTTCCGACGACGCGGACGTCGGCGATGAACTGATTGC 1690       1700       1710       1720       1730       1740       1750
                ....|....|....|....|....|....|....|....|....|....|....|....|....|....|
US8 gene        CATCGCGGACGCACGCGGGGACCCGCCAGAGACCCTGCCCCCCGGCGCGGGCGGCGCCGCGCCCGCGTGC
US8.5 (US8A)    CATCGCGGACGCACGCGGGGACCCGCCAGAGACCCTGCCCCCCGGCGCGGGCGGCGCCGCGCCCGCGTGC 1760       1770       1780       1790       1800       1810       1820
                ....|....|....|....|....|....|....|....|....|....|....|....|....|....|
US8 gene        CGCAGACCACCTCGCGGCGGCTCCCCCGCGGCCTTTCCCGTGGCCCTCCACGCCGTGGACGCCCCCTCCC
US8.5 (US8A)    CGCAGACCACCTCGCGGCGGCTCCCCCGCGGCCTTTCCCGTGGCCCTCCACGCCGTGGACGCCCCCTCCC 1830       1840       1850       1860       1870       1880       1890
                ....|....|....|....|....|....|....|....|....|....|....|....|....|....|
US8 gene        AATTCGTCACCTGGCTCGCCGTGCGCTGGCTGCGGGGGGCGGTGGGTCTCGGGGCCGTCCTGTGCGGGAT
US8.5 (US8A)    AATTCGTCACCTGGCTCGCCGTGCGCTGGCTGCGGGGGGCGGTGGGTCTCGGGGCCGTCCTGTGCGGGAT 1900       1910       1920       1930       1940       1950       1960
                ....|....|....|....|....|....|....|....|....|....|....|....|....|....|
US8 gene        TGCGTTTTACGTGACGTCAATCGCCCGAGGCGCATAAAGGTCCGGCGGCCACCCCGCCGCAGCTCATAAA
US8.5 (US8A)    TGCGTTTTACGTGACGTCAATCGCCCGAGGCGCATAAAGGTCCGGCGGCCACCCCGCCGCAGCTCATAAA 1970       1980       1990       2000       2010       2020       2030
                ....|....|....|....|....|....|....|....|....|....|....|....|....|....|
US8 gene        AATCGTGAGTCACGGCAACCCCACCTTCGCCTCCGCCCTCCGCCAGCGCCCTTCCGCGTCCGCGATGACC
US8.5 (US8A)    AATCGTGAGTCACGGCAACCCCACCTTCGCCTCCGCCCTCCGCCAGCGCCCTTCCGCGTCCGCGATGACC 2040       2050       2060       2070       2080       2090       2100
                ....|....|....|....|....|....|....|....|....|....|....|....|....|....|
US8 gene        TCCCGGCCCGCCGACCAAGACTCGGTGCGTTCCAGCGCGTCGGTGCCGCTTTACCCCGCGGCCTCGCCCG
US8.5 (US8A)    TCCCGGCCCGCCGACCAAGACTCGGTGCGTTCCAGCGCGTCGGTGCCGCTTTACCCCGCGGCCTCGCCCG 2110       2120       2130       2140       2150       2160       2170
                ....|....|....|....|....|....|....|....|....|....|....|....|....|....|
US8 gene        TCCCGGCAGAAGCCTACTACTCGGAAAGCGAAGACGAGGCCGCCAACGACTTCCTCGTGCGCATGGGCCG
US8.5 (US8A)    TCCCGGCAGAAGCCTACTACTCGGAAAGCGAAGACGAGGCCGCCAACGACTTCCTCGTGCGCATGGGCCG
```

FIGURE 2 (continued)

```
                   2180       2190       2200       2210       2220       2230       2240
              ....|....|....|....|....|....|....|....|....|....|....|....|....|....|
US8 gene      CCAGCAGTCGGTCCTAAGGCGCCGACGGCGGCGCACGCGGTGCGTCGGGCTGGTTATCGCCTGTCTCGTC
US8.5 (US8A)  CCAGCAGTCGGTCCTAAGGCGCCGACGGCGGCGCACGCGGTGCGTCGGGCTGGTTATCGCCTGTCTCGTC 2250       2260       2270       2280       2290       2300       2310
              ....|....|....|....|....|....|....|....|....|....|....|....|....|....|
US8 gene      GTGGCCCTCCTATCTGGAGGGTTCGGGGCACTTTTGGTGTGGCTGCTCCGCTAAATGACGCCTCGATGTA
US8.5 (US8A)  GTGGCCCTCCTATCTGGAGGGTTCGGGGCACTTTTGGTGTGGCTGCTCCGCTAAATGACGCCTCGATGTA 2320       2330       2340       2350       2360       2370
              ....|....|....|....|....|....|....|....|....|....|....|....|.
US8 gene      TGGCGCCTTCTTCGCCCCCACCCCTCGCCGCGACCCACGTCCGTATGTTAATTGCAATAAA
US8.5 (US8A)  TGGCGCCTTCTTCGCCCCCACCCCTCGCCGCGACCCACGTCCGTATGTTAATTGCAATAAA
```

FIGURE 2 (continued)

SEQUENCE LISTING

```
<160> NUMBER OF SEQ ID NOS: 25

<210> SEQ ID NO 1
<211> LENGTH: 480
<212> TYPE: DNA
<213> ORGANISM: human herpesvirus 1
<300> PUBLICATION INFORMATION:
<308> DATABASE ACCESSION NUMBER: X14112.1  GI:1944536
<309> DATABASE ENTRY DATE: 1997-04-18
<313> RELEVANT RESIDUES IN SEQ ID NO: (142744)..(143223)

<400> SEQUENCE: 1
atggatccgg ctttgagatc ttatcaccaa cggctccgtc tgtataccccc cgtagcgatg        60 ggcatcaatc tcgccgccag ctcacaacct ttggatccgg aaggcccgat cgccgttact       120
cccaggcctc cgattcgtcc gtcttctggt aaggcgcccc atcccgaggc ccacgtcgg        180 tcgccgaact gggcgaccgc cggcgaggtg gacgtcggag acgagctaat cgcgatttcc       240
gacgaacgcg accccccccg acatgaccgc ccgcccctcg ccacgtcgac cgcgccctcg       300 ccacaccccgc gaccccggg ctacacggcc gttgtctccc cgatggccct ccaggctgtc       360
gacgccccct ccctgtttgt cgcctggctg gccgctcggt ggctccgggg ggcttccggc       420
ctgggggccg tcctgtgtgg gattgcgtgg tatgtgacgt caattgcccg aggcgcataa       480

<210> SEQ ID NO 2
<211> LENGTH: 441
<212> TYPE: DNA
<213> ORGANISM: Human herpesvirus 2
<300> PUBLICATION INFORMATION:
<308> DATABASE ACCESSION NUMBER: NC_001798.1  GI:9629267
<309> DATABASE ENTRY DATE: 2000-08-01
<313> RELEVANT RESIDUES IN SEQ ID NO: (145329)..(145769)

<400> SEQUENCE: 2
atggatccgg ctttgagatc ttatcaccaa cggctccgtc tgtataccccc catagcgagg        60 ggcgtaaatc tcgccgcccg ctcaccacct ttggttcggg aagcccgggc cgtcgtcact       120
cccaggcctc ctatccgtcc gtcctctggt aaggcgtctt ccgacgacgc ggacgtcggc       180
gatgaactga ttgccatcgc ggacgcacgc ggggaccccgc cagagaccct gccccccggc       240
gcgggcggcg ccgcgcccgc gtgccgcaga ccacctcgcg gcggctcccc cgcggccttt       300
cccgtggccc tccacgccgt ggacgccccc tcccaattcg tcacctggct cgccgtgcgc       360
tggctgcggg gggcggtggg tctcggggcc gtcctgtgcg ggattgcgtt ttacgtgacg       420
tcaatcgccc gaggcgcata a                                                  441

<210> SEQ ID NO 3
<211> LENGTH: 58
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (26)..(58)
<223> OTHER INFORMATION: polyd(T) and/or a poly(A) tail

<400> SEQUENCE: 3
```

```
atgcgcctcg ggcgattgac gtcactttaa aaaaaaaaaa aaaaaaaaaa aaaaaaaa          58
```

<210> SEQ ID NO 4
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 4

```
atgcgcctcg ggcgattgac gtcac                                              25
```

<210> SEQ ID NO 5
<211> LENGTH: 57
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (25)..(57)
<223> OTHER INFORMATION: polyd(T) and/or a poly(A) tail

<400> SEQUENCE: 5

```
ggtatacaga cggagccgtt ggtgtttaaa aaaaaaaaaa aaaaaaaaa aaaaaaa            57
```

<210> SEQ ID NO 6
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 6

```
ggtatacaga cggagccgtt ggtg                                               24
```

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 7

```
aggcctccga ttcgtccgtc                                                    20
```

<210> SEQ ID NO 8
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 8

```
cgtccgtctt ctggtaaggc g                                                  21
```

<210> SEQ ID NO 9
<211> LENGTH: 50
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 9

```
aatttaatac gactcactat agggagaatt agctcgtctc cgacgtccac        50

<210> SEQ ID NO 10
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 10
attagctcgt ctccgacgtc cac                                     23

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 11
tcgtcactcc caggcctc                                           18

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 12
aggcctccta tccgtccgtc c                                       21

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 13
cacgtcggtc gccgaact                                           18

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 14
tcggtcgccg aactgggcga                                         20

<210> SEQ ID NO 15
<211> LENGTH: 49
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 15
aatttaatac gactcactat agggagacaa tcagttcatc gccgacgtc         49
```

```
<210> SEQ ID NO 16
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 16
caatcagttc atcgccgacg tc                                              22

<210> SEQ ID NO 17
<211> LENGTH: 48
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 17
aatttaatac gactcactat agggagagcg atggcaatca gttcatcg                  48

<210> SEQ ID NO 18
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 18
gcgatggcaa tcagttcatc g                                               21

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 19
ggtaaggcgt cttccgacga                                                 20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 20
taaggcgtct tccgacgacg                                                 20

<210> SEQ ID NO 21
<211> LENGTH: 47
<212> TYPE: DNA
<213> ORGANISM: Artificial Sequence
<220> FEATURE:
<223> OTHER INFORMATION: Synthetic oligomer
<220> FEATURE:
<221> NAME/KEY: promoter
<222> LOCATION: (1)..(27)

<400> SEQUENCE: 21
aatttaatac gactcactat agggagatcg tctccgacgt ccacctc                   47

<210> SEQ ID NO 22
```

```
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 22
tcgtctccga cgtccacctc                                                   20

<210> SEQ ID NO 23
<211> LENGTH: 2555
<212> TYPE: DNA
<213> ORGANISM: Herpes Simplex Virus 1
<300> PUBLICATION INFORMATION:
<308> DATABASE ACCESSION NUMBER: NC_001806.1
<309> DATABASE ENTRY DATE: 2000-08-01
<313> RELEVANT RESIDUES IN SEQ ID NO: (141139)..(143693)

<400> SEQUENCE: 23
catttaaggc gttgttgtgt tgactttgcc tcttctggcg ggttggtgcg gtgctgtttg        60
ttgggctccc attttacccg aagatcggct gctatcccg ggacatggat cgcggggcgg       120
tggtggggtt tcttctcggt gtttgtgttg tatcgtgctt ggcgggaacg cccaaaacgt      180
cctggagacg ggtgagtgtc ggcgaggacg tttcgttgct tccagctccg gggcctacgg      240
ggcgcggccc gacccagaaa ctactatggg ccgtggaacc cctggatggg tgcggcccct      300
tacacccgtc gtgggtctcg ctgatgcccc ccaagcaggt gcccgagacg tcgtggatg       360 cggcgtgcat gcgcgctccg gtcccgctgg cgatggcgta cgccccccg gccccatctg      420 cgaccggggg tctacgaacg gacttcgtgt ggcaggagcg cgcggccgtg gttaaccgga      480
gtctggttat tcacggggtc cgagagacgg acagcggcct gtataccctg tccgtgggcg      540
acataaagga cccggctcgc caagtggcct cggtggtcct ggtggtgcaa ccggcccag      600 ttccgacccc acccccgacc ccagccgatt acgacgagga tgacaatgac gagggcgagg      660
acgaaagtct cgccggcact cccgccagcg ggacccccg gctcccgcct cccccgccc       720 ccccgaggtc ttggcccagc gcccccgaag tctcacatgt gcgtggggtg accgtgcgta      780
tggagactcc ggaagctatc ctgttttccc ccggggagac gttcagcacg aacgtctcca      840
tccatgccat cgcccacgac gaccagacct actccatgga cgtcgtctgg ttgaggttcg      900
acgtgccgac ctcgtgtgcc gagatgcgaa tatacgaatc gtgtctgtat cacccgcagc      960
tcccagaatg tctgtccccg gccgacgcgc cgtgcgccgc gagtacgtgg acgtctcgcc     1020
tggccgtccg cagctacgcg gggtgttcca gaacaaaccc cccaccgcgc tgttcggccg     1080
aggctcacat ggagcccgtc ccggggctgg cgtggcaggc ggcctccgtc aatctggagt     1140
tccgggacgc gtccccacaa cactccggcc tgtatctgtg tgtggtgtac gtcaacgacc     1200
atattcacgc ctggggccac attaccatca gcaccgcggc gcagtaccgg aacgcggtgg     1260
tggaacagcc cctcccacag cgcggcgcgg atttggccga gcccaccac ccgcacgtcg      1320 gggcccctcc ccacgcgccc ccaacccacg gcgcccctgcg gttaggggcg gtgatggggg     1380
ccgccctgct gctgtctgca ctggggttgt cggtgtgggc gtgtatgacc tgttggcgca     1440
ggcgtgcctg gcgggcggtt aaaagcaggg cctcgggtaa ggggcccacg tacattcgcg     1500
tggccgacag cgagctgtac gcggactgga gctcggacag cgaggagaa cgcgaccagg      1560 tcccgtggct ggccccccg gagagacccg actctccctc caccaatgga tccggctttg      1620
agatcttatc accaacggct ccgtctgtat accccgtag cgatgggcat caatctcgcc      1680
gccagctcac aaccttggga tccggaaggc ccgatcgccg ttactcccag gcctccgatt      1740
```

```
cgtccgtctt ctggtaaggc gccccatccc gaggccccac gtcggtcgcc gaactgggcg    1800
accgccggcg aggtggacgt cggagacgag ctaatcgcga tttccgacga acgcggaccc    1860
ccccgacatg accgcccgcc cctcgccacg tcgaccgcgc cctcgccaca cccgcgaccc    1920
ccgggctaca cggccgttgt ctccccgatg ccctccagg ctgtcgacgc ccctccctg      1980 tttgtcgcct ggctggccgc tcggtggctc cgggggggctt ccggcctggg ggccgtcctg   2040
tgtgggattg cgtggtatgt gacgtcaatt gcccgaggcg cataaagggc cggtggtccg    2100
cctagccgca gcaaattaaa aatcgtgagt cacagcgacc gcaacttccc acccggagct    2160
ttcttccggc ctcgatgacg tcccggctct ccgatcccaa ctcctcagcg cgatccgaca    2220
tgtccgtgcc gctttatccc acggcctcgc cagtttcggt cgaagcctac tactcggaaa    2280
gcgaagacga ggcggccaac gacttcctcg tacgcatggg ccgccaacag tcggtattaa    2340
ggcgtcgacg cagacgcacc cgctgcgtcg gcatggtgat cgcctgtctc ctcgtggccg    2400
ttctgtcggg cggatttggg gcgctcctga tgtggctgct ccgctaaaag accgcatcga    2460
cacgcgcgtc cttcttgtcg tctctcttcc ccccatcac cccgcaattt gcacccagcc     2520
tttaactaca ttaaattggg ttcgattggc aatgt                               2555
```

<210> SEQ ID NO 24
<211> LENGTH: 2371
<212> TYPE: DNA
<213> ORGANISM: Herpes Simplex Virus 2
<300> PUBLICATION INFORMATION:
<308> DATABASE ACCESSION NUMBER: NC_001798.1
<309> DATABASE ENTRY DATE: 2000-08-01
<313> RELEVANT RESIDUES IN SEQ ID NO: (143843)..(146213)

<400> SEQUENCE: 24

```
atggctcgcg gggccgggtt ggtgtttttt gttggagttt gggtcgtatc gtgcctggcg      60
gcagcaccca gaacgtcctg gaaacgggta acctcgggcg aggacgtggt gttgcttccg    120
gcgcccgcgg aacgcacccg ggcccacaaa ctactgtggg ccgcggaacc cctggatgcc    180
tgcggtcccc tgcgcccgtc gtgggtggcg ctgtggcccc ccgacgggt gctcgagacg     240 gtcgtggatg cggcgtgcat gcgcgccccg gaaccgctcg ccatagcata cagtcccccg    300
ttccccgcgg gcgacgaggg actgtattcg gagttggcgt ggcgcgatcg cgtagccgtg    360
gtcaacgaga gtctggtcat ctacggggcc ctggagacgg acagcggtct gtacaccctg    420
tccgtggtcg gcctaagcga cgaggcgcgc caagtggcgt cggtggttct ggtcgtggag    480
cccgcccctg tgccgacccc gacccccgac gactacgacg aagaagacga cgcgggcgtg    540
acgaacgcac gccggtcagc gttcccccc caaccccccc ccgtcgtcc cccgtcgcc      600 ccccgacgc accctcgtgt tatccccgag gtgtcccacg tgcgcggggt aacggtccat     660
atggagaccc tggaggccat tctgtttgcc cccggggaga cgtttgggac gaacgtctcc    720
atccacgcca ttgcccacga cgacggtccg tacgccatgg acgtcgtctg gatgcggttt    780
gacgtgccgt cctcgtgcgc cgatatgcgg atctacgaag cttgtctgta tcacccgcag    840
cttccagagt gtctatctcc ggccgacgcg ccgtgcgccg taagttcctg ggcgtaccgc    900
ctggcggtcc gcagctacgc cggctgttcc aggactacgc ccccgccgcg atgttttgcc    960
gaggctcgca tggaaccggt cccggggttg gcgtggctgg cctccaccgt caatctggaa   1020
ttccagcacg cctcccccca gcacgccggc ctctacctgt gcgtggtgta cgtggacgat   1080
catatccacg cctggggcca catgaccatc agcaccgcgg cgcagtaccg gaacgcggtg   1140
```

```
gtggaacagc acctccccca gcgccagccc gagcccgtcg agcccacccg cccgcacgtg    1200 agagccccccc atcccgcgcc ctccgcgcgc ggcccgctgc gcctcggggc ggtgctgggg    1260
gcggccctgt tgctggccgc cctcgggctg tccgcgtggg cgtgcatgac ctgctggcgc    1320
aggcgctcct ggcgggcggt taaaagccgg gcctcggcga cgggccccac ttacattcgc    1380
gtggcggaca gcgagctgta cgcggactgg agttcggaca gcgaggggga gcgcgacggg    1440
tccctgtggc aggaccctcc ggagagaccc gactctccct ccacaaatgg atccggcttt    1500
gagatcttat caccaacggc tccgtctgta taccccata gcgaggggcg taaatctcgc    1560
cgcccgctca ccacctttgg ttcgggaagc ccgggccgtc gtcactccca ggcctcctat    1620
ccgtccgtcc tctggtaagg cgtcttccga cgacgcggac gtcggcgatg aactgattgc    1680
catcgcggac gcacgcgggg acccgccaga gaccctgccc ccggcgcggg gcggcgccgc    1740
gcccgcgtgc cgcagaccac ctcgcggcgg ctccccgcg gcctttcccg tggccctcca    1800
cgccgtggac gccccctccc aattcgtcac ctggctcgcc gtgcgctggc tgcgggggggc    1860 ggtgggtctc ggggccgtcc tgtgcgggat tgcgttttac gtgacgtcaa tcgcccgagg    1920
cgcataaagg tccggcggcc accccgccgc agctcataaa aatcgtgagt cacggcaacc    1980
ccaccttcgc ctccgccctc cgccagcgcc cttccgcgtc cgcgatgacc tcccggcccg    2040
ccgaccaaga ctcggtgcgt tccagcgcgt cggtgccgct ttaccccgcg gcctcgcccg    2100
tcccggcaga agcctactac tcggaaagcg aagacgaggc cgccaacgac ttcctcgtgc    2160
gcatgggccg ccagcagtcg gtcctaaggc gccgacggcg gcgcacgcgg tgcgtcgggc    2220
tggttatcgc ctgtctcgtc gtggccctcc tatctggagg gttcggggca cttttggtgt    2280
ggctgctccg ctaaatgacg cctcgatgta tggcgccttc ttcgccccca cccctcgccg    2340
cgacccacgt ccgtatgtta attgcaataa a                                   2371
```

<210> SEQ ID NO 25
<211> LENGTH: 950
<212> TYPE: DNA
<213> ORGANISM: Herpes Simplex Virus 1
<300> PUBLICATION INFORMATION:
<308> DATABASE ACCESSION NUMBER: NC_001806.1
<309> DATABASE ENTRY DATE: 2000-08-01
<313> RELEVANT RESIDUES IN SEQ ID NO: (142744)..(143693)

<400> SEQUENCE: 25

```
atggatccgg ctttgagatc ttatcaccaa cggctccgtc tgtataccccc cgtagcgatg     60 ggcatcaatc tcgccgccag ctcacaacct ttggatccgg aaggcccgat cgccgttact    120
cccaggcctc cgattcgtcc gtcttctggt aaggcgcccc atcccgaggc ccacgtcgg    180 tcgccgaact gggcgaccgc cggcgaggtg gacgtcggag acgagctaat cgcgatttcc    240
gacgaacgcg gacccccccg acatgaccgc ccgcccctcg ccacgtcgac cgcgccctcg    300
ccacacccgc gaccccgggg ctacacggcc gttgtctccc cgatggccct ccaggctgtc    360 gacgcccccct ccctgtttgt cgcctggctg gccgctcggt ggctccgggg ggcttccggc    420
ctgggggccg tcctgtgtgg gattgcgtgg tatgtgacgt caattgcccg aggcgcataa    480
agggccggtg gtccgcctag ccgcagcaaa ttaaaaatcg tgagtcacag cgaccgcaac    540
ttcccacccg gagctttctt ccggcctcga tgacgtcccg gctctccgat cccaactcct    600
cagcgcgatc cgacatgtcc gtgccgcttt atcccacggc ctcgccagtt tcggtcgaag    660
cctactactc ggaaagcgaa gacgaggcgg ccaacgactt cctcgtacgc atgggccgcc    720
aacagtcggt attaaggcgt cgacgcagac gcacccgctg cgtcggcatg gtgatcgcct    780
```

```
gtctcctcgt ggccgttctg tcgggcggat ttggggcgct cctgatgtgg ctgctccgct      840
aaaagaccgc atcgacacgc gcgtccttct tgtcgtctct cttccccccc atcacccgc       900 aatttgcacc cagcctttaa ctacattaaa ttgggttcga ttggcaatgt                 950
```

COMPOSITIONS, METHODS AND KITS TO DETECT HERPES SIMPLEX VIRUS NUCLEIC ACID

CROSS-REFERENCE TO RELATED APPLICATIONS

This application is a continuation of U.S. application Ser. No. 14/944,532, filed Nov. 18, 2015, now pending, which is a continuation of U.S. application Ser. No. 13/642,428, filed Oct. 19, 2012, now U.S. Pat. No. 9,206,484, which is the national stage entry under 35 U.S.C. § 371 of International Application No. PCT/US11/33488 filed Apr. 21, 2011, now expired, which claims the benefit of priority under 35 U.S.C. § 119 of U.S. Provisional Application No. 61/326,329, filed on Apr. 21, 2010, the contents of each of which applications are incorporated herein by reference in its entirety.

FIELD

The present invention relates to the detection of infectious agents, more specifically to the detection of Herpes Simplex virus (HSV). Compositions, methods and kits are described for the detection of HSV (including HSV types 1 and 2) by using in vitro nucleic acid amplification techniques.

INTRODUCTION

Herpes simplex virus (HSV) is part of the larger herpes virus family, including Varicella-Zoster virus (VZV), Epstein-Barr virus (EBV) and Cytomegalovirus (CMV). It is an enveloped double-stranded DNA virus causing infections in humans. HSV is classified into various types, including HSV-1 and HSV-2. The complete genomes of human HSV-1 and HSV-2 have been sequenced (see, for example, NCBI Accession Nos. NC_001806.1/GI:9629378 and NC_001798.1/GI:9629267, respectively; see also accession numbers X14112 and Z86099, respectively). Both HSV-1 and HSV-2 can cause disease in humans and exposure or infection is fairly common in adult populations. Up to 80% of the U.S. adult population has been exposed to HSV-1 and approximately 20% of the U.S. population has contracted HSV-2 infections.

Symptoms of HSV infection include the common cold sore found near the lips and also genital herpes. The virus can also cause keratoconjunctivitis, with the potential to lead to blindness, and encephalitis. Once subsided, the virus remains in a latent state inside nerve cells (ganglia) that supply nerve fibres to the infected area. The virus can become reactivated and travels through the nerve fibres back to the skin, thereby causing recurrent disease.

HSV-2 is commonly associated with newborn encephalitis where it is associated with maternal genital infections. HSV-related encephalitis has the highest fatality rate of all types of encephalitis with an annual incidence of 1 to 4 per million. HSV encephalitis affects people of all ages and at any time of the year. In adults, HSV-related encephalitis is thought to be due to a reactivation of a latent virus. Symptoms may include fever, headaches, seizures, an altered level of consciousness and personality changes. The similarity of these symptoms to other maladies makes clinical diagnosis difficult. If left untreated, the mortality rate for Herpes Simplex Encephalitis (HSE) is as high as seventy percent, compared with as low as nineteen percent among those who receive treatment. Of the treated patients, about one third can return to normal function.

One mechanism for transmission of HSV is by sexual transmission. This route of transmission presents a serious consequence of HSV infection in the transmission of the HIV virus. HIV transmission is five times more likely to occur from an HIV/HSV-2-coinfected person with genital ulceration and HIV acquisition is twice as likely in someone sero-positive for HSV-2.

Accurate diagnosis of HSV infection is essential if transmission rates of HSV and its consequences are to be reduced. Although it is not possible to eradicate HSVs from an infected individual, episodic treatment with nucleoside analogue drugs will shorten the duration of the clinical episode and can also reduce the risk of transmission of the virus when continuously administered as daily suppressive therapy. Clinical diagnosis of HSV infection has been reported to have a poor sensitivity of only approximately 40% (*Expert Rev. Mol. Diagn.* 4, 485-493 (2004); *Sex. Trans. Dis.* 17, 90-94 (1990)) so rapid reliable tests with good sensitivity and specificity are needed to improve diagnostic accuracy in those with and without symptoms. Tests are also required that differentiate between HSV-1 and -2.

Current diagnostic methods for HSV include viral culture, serological tests and nucleic acid amplification testing (NAAT).

Culture and typing was once considered the gold standard for diagnosis but its usefulness is severely limited by the stage of clinical disease. When testing early vesicular lesions, the culture detection rate is about 90% whereas in older crusted lesions this falls to only 27% (*Genitourin. Med.* 64, 103-106 (1988)). Another problem with this method is that it is slow since it takes 3 days for the majority of culture isolates to appear positive. The liability of the virus also means that samples must be transported rapidly with maintenance of the cold chain otherwise much reduced sensitivity will result due to, for example, bacterial outgrowth.

Detection of HSV infections has improved dramatically with the advent of type-specific HSV antibody serology testing (*Am. J. Clin. Pathol.* 120, 829-844 (2003). These tests are sensitive and can distinguish between HSV-1 and HSV-2 antibodies. However, type specific antibody tests suffer from false positive results and are also considered inadequate due to a delay of between two and three weeks in appearance of antibody response after initial infection. The performance of the same test can also vary, giving different sensitivities and specificities depending on the population tested (*Clin. Microbiol. Infect.* 10, 530-536 (2004)). For these reasons, they are not considered suitable for general population screening.

NAAT testing for HSV provides for the direct detection of viral DNA from specimens by amplifying DNA sequences using HSV-1 or -2 specific primers and has been shown to be superior to culture (*Sex. Trans. Infect.* 78, 21-25 (2002); *Sex. Trans. Infect.* 80, 406-410 (2004)) and highly specific as compared to cell culture (*J. Infect. Dis.* 1345-1351(2003)). Different HSV genes have been identified as targets for DNA amplification, among them, DNA polymerase glycoprotein. NAAT based testing for HSV has utilised Strand-displacement amplification (SDA), PCR, real time PCR and the TaqMan® PCR detection system. NAAT based assays for HSV are now considered to be the gold standard. However, PCR-based amplification assays are not without their limitations. For example, tests may take up to 2 days to complete and require specialized thermo-cycling equipment.

Sciortino et al. (2001) *J. Virol.* 75, 17 p 8105-8116 describe a method for the detection of HSV using reverse transcribed RNAs that were detected by PCR. A set of 90 primers were designed to amplify all of the 84 expressed ORFs of HSV. One primer pair was designed to amplify a portion of the US8.5 ORF of HSV-1, hybridising to regions 134 to 155 and 461 to 480 of GenBank Accession No: X14112.1, GI:1944536, region: 142744 . . . 143223. Note, the US8.5 is also referred to as US8A, thus these terms are interchangeable. However, the method described therein suffers from the problems associated with PCR-based amplification methodologies and also requires a reverse transcription step which adds yet further complexity to the method. It is also believed that this assay would not be able to discriminate between HSV-1 and HSV-2 nucleic acids.

A need remains for a diagnostic test that provides sensitive and specific detection of HSV in a relatively short time so that infected individuals may be treated promptly to limit morbidity and prevent the spread of infection. A test of this kind that distinguishes between HSV-1 and/or HSV-2 would also be desirable and so a type determination of HSV that is present in the sample can be made.

SUMMARY

The present invention relates to methods, compositions, kits and nucleic acids for determining the presence of HSV, specifically HSV-1 and/or HSV-2, in a sample. The methods involve the amplification of viral nucleic acid to detect the HSV target sequence in the sample. The methods can advantageously provide for the sensitive detection and type-determination of HSV. The present invention is also directed to a method—such as a TMA based method—for the detection of HSV which provides for the direct, rapid, specific and sensitive detection of HSV RNA. Targeting single stranded RNA is beneficial over targeting the double stranded genomic DNA because there is no need for an additional denaturation step which otherwise adds further complexity to the method. The use of RNA can also provide improved amplification oligomer efficiency when methods—such as TMA—start from a single stranded nucleic acid molecule.

The viral nucleic acid that is targeted according to the present invention is the US8.5 open reading frame (ORF) of HSV, which overlaps a portion of the US8 gene of HSV. (Georgopoulou et al. (1993) *J. Virol.* 67 3961-3968). This ORF is present in both HSV-1 and HSV-2 yet its function in the viral life cycle is unknown. It is known that the ORF is not essential for viral replication or packaging but US8.5 RNA is one of the viral RNAs reproducibly detected in all purified virion preparations tested (Sciortino et al. (2001) *J. Virol.* 74, 9078-9082). Chimeric proteins comprising the US8.5 ORF fused to the ORF encoding the enhanced green fluorescent protein were found to be expressed in newly infected cells (Sciortino et al. (2002) *PNAS* 99, 12 p 8318-8323), and when co-infected with the viral UL49 ORF, US8.5 was expressed in uninfected cells co-cultured with infected cells. Thus, US8.5 RNA is transported from infected cells to uninfected cells. This is particularly advantageous in the context of the present invention since it means that target nucleic acid can be detected in virus, in infected cells and in adjacent cells (which is indicative that infection may be spreading), thereby increasing the sensitivity of the methods and allowing for a larger area from which to draw cells that will test positive for an infection. Moreover, the nucleic acid sequence of the US8.5 ORF in HSV-1 and HSV-2 is different. This difference in nucleic acid sequence can be exploited by designing amplification oligomers and/ or nucleic acid probes that are specific for each of the sequences. Thus, the methods of the present invention can be used to distinguish between the two types of HSV. Accordingly, it is possible to determine if a sample comprises HSV-1 or HSV-2 or a combination thereof. DNA sequences encoding the US8.5 ORF from HSV-1 (SEQ ID NO:1) and HSV-2 (SEQ ID NO:2) are shown in Table 2.

FIGS. 1 and 2 further illustrate the US8.5 gene relative to the US8 gene from HSV-1 and HSV-2, respectively. While US8.5 is typically expressed early in the viral lifecycle, the US8 gene is constitutively expressed. Further, the sequence of the US8 gene in HSV-1 and HSV-2 is different. Thus, the methods of the present invention can be used to distinguish between the two types of HSV. Accordingly, it is possible to determine if a sample comprises HSV-1 or HSV-2 or a combination thereof in both early and late stages of the viral lifecycle. DNA sequences US8 from HSV-1 (SEQ ID NO:23) and HSV-2 (SEQ ID NO:24) are shown in Table 2.

In one aspect, there is provided a method for specifically detecting a Herpes Simplex Virus (HSV) target nucleic acid in a sample comprising the steps of: (a) providing a sample suspected of containing at least a HSV target nucleic acid; (b) contacting said sample with at least two amplification oligomers, wherein a first of said amplification oligomers comprises a target hybridizing sequence 15 to 45 nucleotides in length and configured to target a sequence in a region of the HSV US8.5 ORF corresponding to either nucleotides 124 to 156 of SEQ ID NO:1 or nucleotides 113 to 144 of SEQ ID NO:2, and wherein a second of said amplification oligomers comprises a target hybridizing sequence 15 to 45 nucleotides in length and configured to target a sequence in a region of the HSV US8.5 ORF corresponding to either nucleotides 205 to 230 of SEQ ID NO:1, or nucleotides 172 to 200 of SEQ ID NO:2; and (c) performing a nucleic acid detection reaction that detects said amplification product to determine whether a HSV target nucleic acid is present in said sample.

In one embodiment, said first of said amplification oligomers comprises, consists or consists essentially of a target hybridizing sequence configured to target a sequence in a region corresponding to nucleotides 124 to 143 or nucleotides 136 to 156 of SEQ ID NO:1.

In another embodiment, said amplification oligomer configured to target a sequence in a region corresponding to nucleotides 124 to 143 of SEQ ID NO:1 comprises, consists or consists essentially of the sequence set forth in SEQ ID NO:7.

In another embodiment, said amplification oligomer is configured to target a sequence in a region corresponding to nucleotides 136 to 156 of SEQ ID NO:1 comprises, consists or consists essentially of the sequence set forth in SEQ ID NO:8.

In another embodiment, said first of said amplification oligomers comprises, consists or consists essentially of a target hybridizing sequence configured to target a sequence in a region corresponding to nucleotides 113 to 130 or nucleotides 124 to 144 of SEQ ID NO:2.

In another embodiment, said amplification oligomer configured to target a sequence in a region corresponding to nucleotides 113 to 130 of SEQ ID NO:2 comprises, consists or consists essentially of the sequence set forth in SEQ ID NO:11.

In another embodiment, said amplification oligomer configured to target a sequence in a region corresponding to nucleotides 124 to 144 of SEQ ID NO:2 comprises, consists or consists essentially of the sequence set forth in SEQ ID NO:12.

In another embodiment, said second of said amplification oligomers configured to target a sequence in a region corresponding to nucleotides 205 to 224 of SEQ ID NO:1 comprises, consists or consists essentially of the sequence set forth in SEQ ID NO:22.

In another embodiment, said second of said amplification oligomers configured to target a sequence in a region corresponding to nucleotides 208 to 230 of SEQ ID NO:1 comprises, consists or consists essentially of the sequence set forth in SEQ ID NO:10.

In another embodiment, said second of said amplification oligomers comprises, consists or consists essentially of a target hybridizing sequence configured to target a sequence in a region corresponding to nucleotides 172 to 193 or nucleotides 180 to 200 of SEQ ID NO:2.

In another embodiment, said second amplification oligomer configured to target a sequence in a region corresponding to nucleotides 172 to 193 of SEQ ID NO:2 comprises, consists or consists essentially of the sequence set forth in SEQ ID NO:16.

In another embodiment, said second amplification oligomer configured to target a sequence in a region corresponding to nucleotides 180 to 200 of SEQ ID NO:2 comprises, consists or consists essentially of the sequence set forth in SEQ ID NO:18.

In another embodiment, said second of said amplification oligomers further comprises a 5' promoter sequence.

In another embodiment, the promoter is a T7 promoter.

In another embodiment, said second of said amplification oligomers configured to target a sequence in a region corresponding to nucleotides 205 to 224 of SEQ ID NO:1 and additionally comprising a 5' promoter sequence comprises, consists or consists essentially of the sequence set forth in SEQ ID NO:21.

In another embodiment, said second of said amplification oligomers configured to target a sequence in a region corresponding to nucleotides 208 to 230 of SEQ ID NO:1 and additionally comprising a 5' promoter sequence comprises, consists or consists essentially of the sequence set forth in SEQ ID NO:9.

In another embodiment, said second of said amplification oligomers comprises, consists or consists essentially of a target hybridizing sequence configured to target a sequence in a region corresponding to nucleotides 172 to 193 of SEQ ID NO:2 and additionally comprising a 5' promoter sequence comprises, consists or consists essentially of the sequence set forth in SEQ ID NO:15.

In another embodiment, said second of said amplification oligomers comprises, consists or consists essentially of a target hybridizing sequence configured to target a sequence in a region corresponding to nucleotides 180 to 200 of SEQ ID NO:2 and additionally comprising a 5' promoter sequence comprises, consists or consists essentially of the sequence set forth in SEQ ID NO:17.

In another embodiment, said detection step comprises contacting said amplification product with a detection probe configured to hybridize to a portion of said amplification product.

In another embodiment, said detection is real-time detection.

In another embodiment, said detection probe is configured to detect a sequence in a region corresponding to nucleotides 173 to 196 of SEQ ID NO:1.

In another embodiment, said detection probe is configured to target a sequence in a region corresponding to nucleotides 173 to 190 or nucleotides 177 to 196 of SEQ ID NO:1.

In another embodiment, said detection probe configured to target a sequence in a region corresponding to nucleotides 173 to 190 of SEQ ID NO:1 comprises, consists or consists essentially of the sequence set forth in SEQ ID NO:13.

In another embodiment, said detection probe configured to target a sequence in a region corresponding to nucleotides 177 to 196 of SEQ ID NO:1 comprises, consists or consists essentially of the sequence set forth in SEQ ID NO:14.

In another embodiment, said detection probe specifically hybridises to HSV-1 target nucleic acid and does not specifically hybridise to HSV-2 target nucleic acid.

In another embodiment, said detection probe is configured to detect a sequence in a region corresponding to nucleotides 148 to 169 of SEQ ID NO:2.

In another embodiment, said detection probe is configured to target a sequence in a region corresponding to nucleotides 148 to 167 of SEQ ID NO:2.

In another embodiment, said detection probe configured to target a sequence in a region corresponding to nucleotides 148 to 167 of SEQ ID NO:2 comprises, consists or consists essentially of the sequence set forth in SEQ ID NO:19.

In another embodiment, said detection probe is configured to target a sequence in a region corresponding to nucleotides 150 to 169 of SEQ ID NO:2.

In another embodiment, said detection probe configured to target a sequence in a region corresponding to nucleotides 150 to 169 of SEQ ID NO:2 comprises, consists or consists essentially of the sequence set forth in SEQ ID NO: 20.

In another embodiment, said detection probe specifically hybridises to HSV-2 target nucleic acid and does not specifically hybridise to HSV-1 target nucleic acid.

In another embodiment, the method further comprises the step of contacting said sample with a target capture oligomer.

In another embodiment, the target capture oligomer is configured to target a sequence in a conserved region between HSV-1 and HSV-2.

In another embodiment, the target capture oligomer is configured to target a sequence in a conserved region between HSV-1 and HSV-2, the region corresponding to nucleotides 25 to 48 of SEQ ID NO:1 or 2.

In another embodiment, the target capture oligomer is configured to target a sequence in a conserved region between HSV-1 and HSV-2, the region corresponding to nucleotides 454 to 478 of SEQ ID NO:1 or corresponding to nucleotides 415 to 439 of SEQ ID NO:2.

In another embodiment, the target capture oligomer comprises, consists or consists essentially of a target hybridizing sequence as set forth in SEQ ID No: 4 or SEQ ID No: 6.

In another embodiment, said target capture oligomer comprises a polyd(T) and/or a poly(A) tail.

In another embodiment, said target capture oligomer comprises, consists or consists essentially of the sequence set forth in SEQ ID No: 3 or SEQ ID No: 5.

In another embodiment, said sample comprises nucleic acid from HSV-1 and/or HSV-2.

In a further aspect, there is provided a method for specifically detecting a HSV-1 target nucleic acid in a sample comprising the steps of: (a) providing a sample suspected of containing at least a HSV target nucleic acid; (b) contacting said sample with at least two amplification oligomers, wherein a first of said amplification oligomers comprises a target hybridizing sequence 15 to 45 nucleotides in length comprising, consisting or consisting essentially of the sequence set forth in SEQ ID NOS:7, 8, 11 or 12; and wherein a second of said amplification oligomers comprises a target hybridizing sequence 15 to 45 nucleotides in length comprising, consisting or consisting essentially of the sequence set forth in SEQ ID NOS:10, 22, 16 or 18; and (c)

performing a nucleic acid detection reaction that detects said amplification product to determine whether a HSV-1 target nucleic acid is present in said sample, wherein said detection probe is configured to detect a sequence in a region corresponding to nucleotides 124 to 230 of SEQ ID NO:1.

In one embodiment, said detection probe oligomer comprises a target hybridizing region that is 15 to 45 nucleotides in length and is configured to target a sequence in an amplicon generated at step b., and corresponding to nucleotides 173 to 196 of SEQ ID NO:1.

In another embodiment, said detection probe is configured to target a sequence in a region corresponding to nucleotides 173 to 190 or nucleotides 177 to 196 of SEQ ID NO:1.

In another embodiment, said detection probe configured to target a sequence in a region corresponding to nucleotides 173 to 190 of SEQ ID NO:1 comprises, consists or consists essentially of the sequence set forth in SEQ ID NO:13.

In another embodiment, said detection probe configured to target a sequence in a region corresponding to nucleotides 177 to 196 of SEQ ID NO:1 comprises, consists or consists essentially of the sequence set forth in SEQ ID NO:14.

In a further aspect, there is provided a method for specifically detecting a HSV-2 target nucleic acid in a sample comprising the steps of: (a) providing a sample suspected of containing at least a HSV target nucleic acid; (b) contacting said sample with at least two amplification oligomers, wherein a first of said amplification oligomers comprises a target hybridizing sequence 15 to 45 nucleotides in length and comprising, consisting or consisting essentially of the sequence set forth in SEQ ID NOS:7, 8, 11 or 12; and wherein a second of said amplification oligomers comprises a target hybridizing sequence 15 to 45 nucleotides in length comprising, consisting or consisting essentially of the sequence set forth in SEQ ID NOS:10, 22, 16 or 18; and (c) performing a nucleic acid detection reaction that detects said amplification product to determine whether a HSV-2 target nucleic acid is present in said sample, wherein said detection probe is configured to detect a sequence in a region corresponding to nucleotides 113 to 200 of SEQ ID NO:2.

In one embodiment, said detection probe oligomer comprises a target hybridizing region that is 15 to 45 nucleotides in length and is configured to target a sequence in an amplicon generated at step b., and corresponding to nucleotides 148 to 169 of SEQ ID NO:2.

In another embodiment, said detection probe is configured to target a sequence in a region corresponding to nucleotides 148 to 167 of SEQ ID NO:2.

In another embodiment, said detection probe configured to target a sequence in a region corresponding to nucleotides 148 to 167 of SEQ ID NO:2 comprises, consists or consists essentially of the sequence set forth in SEQ ID NO:19.

In another embodiment, said detection probe is configured to target a sequence in a region corresponding to nucleotides 150 to 169 of SEQ ID NO:2.

In another embodiment, said detection probe configured to target a sequence in a region corresponding to nucleotides 150 to 169 of SEQ ID NO:2 comprises, consists or consists essentially of the sequence set forth in SEQ ID NO: 20.

In a further aspect, there is provided a method for specifically detecting a HSV-1 and a HSV-2 target nucleic acid in a sample comprising the steps of: (a) providing a sample suspected of containing at least a HSV target nucleic acid; (b) contacting said sample with at least two amplification oligomers, wherein a first of said amplification oligomers comprises a target hybridizing sequence 15 to 45 nucleotides in length and comprising, consisting or consisting essentially of the sequence set forth in SEQ ID NOS:7, 8, 11 or 12; and wherein a second of said amplification oligomers comprises a target hybridizing sequence 15 to 45 nucleotides in length comprising, consisting or consisting essentially of the sequence set forth in SEQ ID NOS:10, 22, 16 or 18; and (c) performing a nucleic acid detection reaction that detects said amplification product to determine whether a HSV-1 and/or a HSV-2 target nucleic acid is present in said sample, wherein said detection probe is configured to detect a sequence in an amplicon that corresponds to nucleotides 124 to 230 of SEQ ID NO:1 and corresponds to nucleotides 113 to 200 of SEQ ID NO:2 and that is substantially conserved between SEQ ID NOS:1 and 2.

In a further aspect, there is provided a composition for use in a HSV target nucleic acid amplification assay comprising at least two amplification oligomers capable of stably hybridizing to a HSV US8.5 target nucleic acid, wherein a first of said amplification oligomers comprises a target hybridizing sequence 15 to 45 nucleotides in length and configured to target a sequence in a region of the HSV US8.5 corresponding to either nucleotides 124 to 156 of SEQ ID NO:1 or nucleotides 113 to 144 of SEQ ID NO:2 and wherein a second of said amplification oligomers comprises a target hybridizing sequence 15 to 45 nucleotides in length and configured to target a sequence in a region of the HSV US8.5 ORF corresponding to either nucleotides 205 to 230 of SEQ ID NO:1 or nucleotides 172 to 200 of SEQ ID NO:2.

In one embodiment, said first of said amplification oligomers comprises, consists or consists essentially of a target hybridizing sequence configured to target a sequence in a region corresponding to nucleotides 124 to 143 or nucleotides 136 to 156 of SEQ ID NO:1.

In another embodiment, said amplification oligomer configured to target a sequence in a region corresponding to nucleotides 124 to 143 of SEQ ID NO:1 comprises, consists or consists essentially of the sequence set forth in SEQ ID NO:7.

In another embodiment, said amplification oligomer configured to target a sequence in a region corresponding to nucleotides 136 to 156 of SEQ ID NO:1 comprises, consists or consists essentially of the sequence set forth in SEQ ID NO:8.

In another embodiment, said first of said amplification oligomers comprises, consists or consists essentially of a target hybridizing sequence configured to target a sequence in a region corresponding to nucleotides 113 to 130 or nucleotides 124 to 144 of SEQ ID NO:2.

In another embodiment, said amplification oligomer configured to target a sequence in a region corresponding to nucleotides 113 to 130 of SEQ ID NO:2 comprises, consists or consists essentially of the sequence set forth in SEQ ID NO:11.

In another embodiment, said amplification oligomer configured to target a sequence in a region corresponding to nucleotides 124 to 144 of SEQ ID NO:2 comprises, consists or consists essentially of the sequence set forth in SEQ ID NO:12.

In another embodiment, said second of said amplification oligomers configured to target a sequence in a region corresponding to nucleotides 205 to 224 of SEQ ID NO:1 comprises, consists or consists essentially of the sequence set forth in SEQ ID NO:22.

In another embodiment, said second of said amplification oligomers configured to target a sequence in a region corresponding to nucleotides 208 to 230 of SEQ ID NO:1 comprises, consists or consists essentially of the sequence set forth in SEQ ID NO:10.

In another embodiment, said second of said amplification oligomers comprises, consists or consists essentially of a target hybridizing sequence configured to target a sequence in a region corresponding to nucleotides 172 to 193 or nucleotides 180 to 200 of SEQ ID NO:2.

In another embodiment, said second amplification oligomer configured to target a sequence in a region corresponding to nucleotides 172 to 193 of SEQ ID NO:2 comprises, consists or consists essentially of the sequence set forth in SEQ ID NO:16.

In another embodiment, said second amplification oligomer configured to target a sequence in a region corresponding to nucleotides 180 to 200 of SEQ ID NO:2 comprises, consists or consists essentially of the sequence set forth in SEQ ID NO:18.

In another embodiment, said second of said amplification oligomers further comprises a 5' promoter sequence.

In another embodiment, the promoter is a T7 promoter.

In another embodiment, said second of said amplification oligomers configured to target a sequence in a region corresponding to nucleotides 205 to 224 of SEQ ID NO:1 and additionally comprising a 5' promoter sequence comprises, consists or consists essentially of the sequence set forth in SEQ ID NO:21.

In another embodiment, said second of said amplification oligomers configured to target a sequence in a region corresponding to nucleotides 208 to 230 of SEQ ID NO:1 and additionally comprising a 5' promoter sequence comprises, consists or consists essentially of the sequence set forth in SEQ ID NO:9.

In another embodiment, said second of said amplification oligomers comprises, consists or consists essentially of a target hybridizing sequence configured to target a sequence in a region corresponding to nucleotides 172 to 193 of SEQ ID NO:2 and additionally comprising a 5' promoter sequence comprises, consists or consists essentially of the sequence set forth in SEQ ID NO:15.

In another embodiment, said second of said amplification oligomers comprises, consists or consists essentially of a target hybridizing sequence configured to target a sequence in a region corresponding to nucleotides 180 to 200 of SEQ ID NO:2 and additionally comprising a 5' promoter sequence comprises, consists or consists essentially of the sequence set forth in SEQ ID NO:17.

In another embodiment, the composition further comprises a detection probe oligomer.

In another embodiment, said detection probe is configured to detect a sequence in a region corresponding to nucleotides 181 to 214 of SEQ ID NO:1.

In another embodiment, said detection probe is configured to target a sequence in a region corresponding to nucleotides 173 to 190 or nucleotides 177 to 196 of SEQ ID NO:1.

In another embodiment, said detection probe configured to target a sequence in a region corresponding to nucleotides 173 to 190 of SEQ ID NO:1 comprises, consists or consists essentially of the sequence set forth in SEQ ID NO:13.

In another embodiment, said detection probe configured to target a sequence in a region corresponding to nucleotides 177 to 196 of SEQ ID NO:1 comprises, consists or consists essentially of the sequence set forth in SEQ ID NO:14.

In another embodiment, said detection probe is configured to detect a sequence in a region corresponding to nucleotides 148 to 169 of SEQ ID NO:2.

In another embodiment, said detection probe is configured to target a sequence in a region corresponding to nucleotides 148 to 167 of SEQ ID NO:2.

In another embodiment, said detection probe configured to target a sequence in a region corresponding to nucleotides 148 to 167 of SEQ ID NO:2 comprises, consists or consists essentially of the sequence set forth in SEQ ID NO:19.

In another embodiment, said detection probe is configured to target a sequence in a region corresponding to nucleotides 150 to 169 of SEQ ID NO:2.

In another embodiment, said detection probe configured to target a sequence in a region corresponding to nucleotides 150 to 169 of SEQ ID NO:2 comprises, consists or consists essentially of the sequence set forth in SEQ ID NO: 20.

In another embodiment, the composition further comprises a target capture oligomer.

In another embodiment, the target capture oligomer is configured to target a sequence in a conserved region between HSV-1 and HSV-2.

In another embodiment, the target capture oligomer is configured to target a sequence in a conserved region between HSV-1 and HSV-2, the region corresponding to nucleotides 25 to 48 of SEQ ID NO:1 or 2.

In another embodiment, the target capture oligomer is configured to target a sequence in a conserved region between HSV-1 and HSV-2, the region corresponding to nucleotides 454 to 478 of SEQ ID NO:1 or corresponding to nucleotides 415 to 439 of SEQ ID NO:2.

In another embodiment, said target capture oligomer comprises, consists or consists essentially of a target hybridizing sequence as set forth in SEQ ID No: 4 or SEQ ID No: 6.

In another embodiment, said target capture oligomer comprises a polyd(T) and/or a poly(A) tail.

In another embodiment, said target capture oligomer comprises, consists or consists essentially of the sequence set forth in SEQ ID No: 3 or SEQ ID No: 5.

In a further aspect, there is provided a kit comprising the composition and optionally a set of instructions for performing same.

In a further aspect, there is provided an isolated DNA sequence (eg. oligomer) comprising, consisting or consisting essentially of a sequence selected from the group consisting of: SEQ ID Nos: 3, 4, 5, 6, 7, 8, 9, 10, 11, 12, 13, 14, 15, 16, 17, 18, 19, 20, 21 and 22 or the corresponding isolated RNA sequence.

In a further aspect, there is provided an isolated DNA sequence comprising, consisting or consisting essentially of the sequence set forth in SEQ ID No: 3, 4, 5, 6, 7, 8, 9, 10, 11, 12, 13, 14, 15, 16, 17, 18, 19, 20, 21 or 22 or the corresponding isolated RNA sequence.

In one embodiment, said sequence is the complement or the reverse complement thereof.

In a further aspect, there is provided a composition for a sequencing reaction to identify the presence or absence of HSV-1 and/or HSV-2 in a sample, wherein said composition comprises an HSV nucleic acid corresponding to nucleotides 124 to 230 of SEQ ID NO:1 corresponding to nucleotides 113 to 200 of SEQ ID NO:2.

In one embodiment, the composition for a sequencing reaction further comprises a non-HSV nucleic acid sequence, such as an adapter sequence, a SMRTBell, a nucleic acid tag sequence or some other sequence that is exogenous to the HSV nucleic acid corresponding to nucleotides 124 to 230 of SEQ ID NO:1 corresponding to nucleotides 113 to 200 of SEQ ID NO:2.

In a further aspect, there is provided a composition for a reaction to identify the presence or absence of HSV-1 and/or HSV-2 in a sample, wherein said composition comprises an HSV nucleic acid corresponding to nucleotides 124 to 230 of SEQ ID NO:1 or corresponding to nucleotides 113 to 200 of SEQ ID NO:2.

In one embodiment, the composition is detected using an amplification and detection technology such as an isothermal amplification like TMA, NASBA, SDA, and the composition is detected in an end-point detection reaction like chemiluminescent detection probe mediated detection. In another embodiment, the composition is detected using an amplification and detection technology such as an isothermal amplification like TMA, NASBA, SDA, and the composition is detected in a real time detection assay like incorporating binding agents into the amplification reaction, incorporating intercalating dyes into the amplification reaction, or incorporating real-time detection probes into the amplification reaction.

In one embodiment, there is an isolated nucleic acid sequence substantially corresponding to, comprising, consisting or consisting essentially of a nucleic acid sequence corresponding to nucleotides 124 to 230 of SEQ ID NO:1 or corresponding to nucleotides 113 to 200 of SEQ ID NO:2.

In one aspect, the isolated nucleic acid sequence is the complement or the reverse complement thereof. In another aspect, the isolated nucleic acid sequence is RNA. In another aspect, the isolated nucleic acid sequence is double stranded DNA. In another aspect, the double stranded DNA is joined at the 5'-end of one strand to the 3'-end of the other strand using an adapter. In another aspect, the double stranded DNA is joined at the 5'-end of the first strand to the 3'-end of the second strand using an adapter, and at the 3'-end of the first strand to the 5'-end of the second strand using an adapter. In a further aspect, the double stranded DNA is circularized using adapters joined to each end of the double stranded DNA. In a further aspect, the adapter is a SMRT-Bell.

BRIEF DESCRIPTION OF THE FIGURES

FIG. 1 is an alignment illustrating the relation of the US8 and the US8.5 (US8A) genes from a representative HSV-1 sequence (SEQ ID NOS:23 and 25). The representative HSV-1 sequence is GenBank Accession Number NC_001806.1 GI:9629378. For this representative sequence, the US8 gene is at residues 141139 to 143693 of the genome and the US8.5 gene is at residues 142744 to 143693 of the genome. US8 is constitutively expressed throughout the viral lifecycle, while US8.5 is expressed in an early stage of the viral lifecycle.

FIG. 2 is an alignment illustrating the relation of the US8 and the US8.5 (US8A) genes from a representative HSV-2 sequence (SEQ ID NOS:24 and 2). The representative HSV-2 sequence is GenBank Accession Number NC_001798.1 GI:9629267. For this representative sequence, the US8 gene is at residues 143843 to 146213 of the genome and the US8.5 gene is at residues 145329 to 146213 of the genome. US8 is constitutively expressed throughout the viral lifecycle, while US8.5 is expressed in an early stage of the viral lifecycle.

DETAILED DESCRIPTION

Nucleic acid oligomer sequences are disclosed that may serve as primers for amplification of HSV nucleic acids, including HSV-1 and/or HSV-2 nucleic acids. The HSV nucleic acids may be detected in a sample by using methods of in vitro nucleic acid amplification, preferably by using a transcription-mediated amplification reaction such as TMA or NASBA, and probes for detection of the amplified nucleic acid sequences. Detection probes hybridize specifically to a portion of the amplified viral sequence, either after completion of or during the amplification process. In one embodiment, the detection probes hybridize specifically to a portion of the amplified HSV-1 or HSV-2 sequence, either after completion of or during the amplification process. The detection probes are able to discriminate between HSV-1 and HSV-2 nucleic acids and so it is possible to determine if either HSV-1 and/or HSV-2 nucleic acid is present in the sample under test. Some embodiments detect the amplified products by using a homogeneous detection method that detects, in a mixture, a labeled probe bound specifically to an amplified sequence (eg., see Arnold et al., 1989, *Clin. Chem.* 35:1588-1594; U.S. Pat. No. 5,658,737, Nelson et al., and U.S. Pat. Nos. 5,118,801 and 5,312,728, Lizardi et al.). Embodiments of the methods also use oligonucleotide sequences that serve as capture probes for processing a sample to capture the target HSV nucleic acid and separate it from other sample components (eg. see U.S. Pat. Nos. 6,110,678, 6,280,952 and 6,534,273).

Methods disclosed herein can be used to detect HSV nucleic acids present in samples from or derived from animals and humans, preferably from biopsies of genital lesions, anogenital lesions, oral lesions, mucocutanoeus lesions, skin lesions, ocular lesions and other types of biological samples as described herein—such as cerebrospinal fluid.

Compositions disclosed herein include amplification oligomers that can be used to specifically amplify selected nucleic acid sequences present in HSV genomic sequences, and nucleic acid probes for detecting the amplified sequences. Preferred embodiments include specific combinations of oligomers to amplify and detect HSV-1 and/or HSV-2 sequences in assays that provide a detectable signal or response within about 45 minutes from beginning of a transcription-associated amplification reaction.

The disclosed nucleic acid sequences and methods are useful for amplifying and detecting HSV nucleic acids from or derived from viral particles present in a sample in a relatively short time so that diagnosis can be made quickly and so effective treatment can be initiated and spread of the virus limited. The methods are useful for screening for individuals who have HSV infections but who do not exhibit definitive symptoms, or who have not seroconverted, and are particularly useful for screening patients who have a higher risk of death or serious complications from HSV infections, eg., young, elderly, or immunocompromised individuals. The methods are also useful for rapid screening of many samples. The methods are useful because they minimize the risk of exposure of laboratory personnel to the infectious HSV agents, thereby limiting the risk of infection and spread of the virus. Thus, the methods and compositions disclosed herein respond to a need for rapid, sensitive, and specific testing of clinical samples that may contain HSV.

To aid in understanding aspects of the disclosure, some terms used herein are described in more detail. All other scientific and technical terms used herein have the same meaning as commonly understood by those skilled in the relevant art, such as may be provided in *Dictionary of Microbiology and Molecular Biology*, 2nd ed. (Singleton et al., 1994, John Wiley & Sons, New York, N.Y.), *The Harper Coffins Dictionary of Biology* (Hale & Marham, 1991, Harper Perennial, New York, N.Y.), and references cited herein. Unless mentioned otherwise, the techniques employed or contemplated herein are standard methods well known to a person of ordinary skill in the art of molecular biology.

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

Sample. A "sample" or "specimen", including "biological" or "clinical" samples may contain or may be suspected of containing HSV or components thereof, such as nucleic acids or fragments of nucleic acids. A sample may be a complex mixture of components. Samples include "biological samples" which include any tissue or material derived from a living or dead mammal or organism, including, eg., blood, plasma, serum, blood cells, saliva, and mucous, cerebrospinal fluid (to diagnose HSV infections of the central nervous system) and samples—such as biopsies—from or derived from genital lesions, anogenital lesions, oral lesions, mucocutanoeus lesions, skin lesions and ocular lesions or combinations thereof. Samples may also include samples of in vitro cell culture constituents including, eg., conditioned media resulting from the growth of cells and tissues in culture medium. The sample may be treated to physically or mechanically disrupt tissue or cell structure to release intracellular nucleic acids into a solution which may contain enzymes, buffers, salts, detergents and the like, to prepare the sample for analysis. In one step of the methods described herein, a sample is provided that is suspected of containing at least a HSV target nucleic acid. Accordingly, this step excludes the physical step of obtaining the sample from a subject.

Nucleic acid. This refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; *The Biochemistry of the Nucleic Acids* 5-36, Adams et al., ed., 11th ed., 1992, Abraham et al., 2007, BioTechniques 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., 2004, *Biochemistry* 43(42):13233-41). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

Polynucleotide. The term denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

Nucleotide. This is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me, or 2' methoxy). As used herein, methoxy oligonucleotides containing "T" residues have a methoxy group at the 2' position of the ribose moiety, and a uracil at the base position of the nucleotide.

Non-nucleotide unit. This is a unit that does not significantly participate in hybridization of a polymer. Such units must not, for example, participate in any significant hydrogen bonding with a nucleotide, and would exclude units having as a component one of the five nucleotide bases or analogs thereof.

Target nucleic acid. This is a nucleic acid comprising a "target sequence" to be amplified. Target nucleic acids may be DNA or RNA and may be either single-stranded or double-stranded. In a preferred embodiment of the invention, the target nucleic acid is RNA. In a more preferred embodiment, the target sequence is RNA encoded by at least a portion of either or both of the DNA sequences set forth in Table 2. The target nucleic acid may include other sequences besides the target sequence that may be amplified. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA. In the instant disclosure, target nucleic acids are nucleic acids—such as DNA or RNA—from HSV, including HSV-1 and/or HSV-2. In a preferred embodiment, the target nucleic acid is RNA from HSV, including HSV-1 and/or HSV-2. In another preferred embodiment, the target nucleic acid comprises RNA encoded by the DNA sequences set forth in SEQ ID NO:1 (HSV-1) or SEQ ID NO:2 (HSV-2) (see Table 2). In another preferred embodiment, the target nucleic acid is RNA from HSV that has not been obtained by reverse transcription of HSV DNA. In other words, according to this embodiment, the target nucleic acid is RNA obtained directly from the virus or a cell infected with same.

Target sequence. This term refers to the particular nucleotide sequence of the target nucleic acid that is to be amplified. Where the target nucleic acid is originally single-stranded, the term "target sequence" will also refer to the sequence complementary to the target sequence as present in the target nucleic acid. Where the target nucleic acid is originally double-stranded, the term "target sequence" refers to both the sense (+) and antisense (−) strands. In choosing a target sequence, the skilled artisan will understand that a sequence should be chosen so as to distinguish between unrelated or closely related target nucleic acids.

The terms "target(s) a sequence" or "target(s) a target nucleic acid" as used herein in reference to a region of HSV nucleic acid refers to a process whereby an oligonucleotide stably hybridizes to the target sequence in a manner that allows for amplification and/or detection as described herein. In one embodiment, the oligonucleotide is complementary to the targeted HSV nucleic acid sequence and contains no mismatches. In another embodiment, the oligonucleotide is complementary but contains 1; or 2; or 3; or 4; or 5 mismatches with the targeted HSV nucleic acid sequence. Preferably, the oligonucleotide that stably hybridizes to the HSV nucleic acid sequence includes at least 10, 11, 12, 13, 14, 15, 16, 17, 18, 19, 20, 21, 22, 23, 24, 25, 30, 35, 40, 45 or 50 nucleotides complementary to the target sequence. It is understood that at least 10 and as many as 50 is an inclusive range such that 10, 50 and each whole number there between are included. The term "configured to target a sequence" as used herein means that the target hybridizing region of an amplification oligonucleotide is designed to have a polynucleotide sequence that could target a sequence of the referenced HSV region, particularly, the referenced HSV-1 or HSV-2 region. Such an amplification oligonucleotide is not limited to targeting that sequence only, but is rather useful as a composition, in a kit or in a method for targeting a HSV target nucleic acid, as is described herein. The term "configured to" denotes an actual arrangement of the polynucleotide sequence configuration of the amplification oligonucleotide target hybridizing sequence.

Isolated. This is meant that a nucleic acid is taken from its natural milieu, but the term does not connote any degree of purification.

Fragment. This term as used herein in reference to the HSV targeted nucleic acid sequence refers to a piece of contiguous nucleic acid. In certain embodiments, the fragment includes contiguous nucleotides from a HSV target nucleic acid, wherein the number of contiguous nucleotides in the fragment are less than that for the entire US8.5 ORF.

Region. This term refers to a portion of a nucleic acid wherein said portion is smaller than the entire nucleic acid. For example, when the nucleic acid in reference is an oligonucleotide promoter provider, the term "region" may be used refer to the smaller promoter portion of the entire oligonucleotide. Similarly, and also as example only, when the nucleic acid is a target nucleic acid, the term "region" may be used to refer to a smaller area of the nucleic acid.

Oligonucleotide. This term may be used interchangeably with "oligomer and "oligo" and refers to a nucleic acid having generally less than 1,000 nucleotide (nt) residues, including polymers in a range of from about 5 nt residues to about 900 nt residues, from about 10 nt residues to about 800 nt residues with a lower limit of about 12 to 15 nt and an upper limit of about 40 to 600 nt, and other embodiments are in a range having a lower limit of about 15 to 20 nt and an upper limit of about 22 to 100 nt. It is understood that these ranges are exemplary only, and an oligonucleotide may contain each whole number included in the range. Oligonucleotides may be purified from naturally occurring sources, but may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase, it may provide a promoter if it contains a sequence recognized by an RNA polymerase and allows for transcription (eg., a T7 provider), and it may function to prevent hybridization or impede primer extension if appropriately situated and/or modified.

As used herein, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

Corresponds. As used herein, a nucleic acid "corresponds" to a specified nucleic acid if the nucleic acid is 100% identical or complementary to the specified nucleic acid.

Substantially corresponding to. As used herein, a nucleic acid "substantially corresponding to" a specified nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. Substantially corresponding nucleic acids vary by at least one nucleotide from the specified nucleic acid. This variation may be stated in terms of a percentage of identity or complementarity between the nucleic acid and the specified nucleic acid. Thus, nucleic acid substantially corresponds to a reference nucleic acid sequence if these percentages of base identity or complementarity are from less than 100% to about 80%. In preferred embodiments, the percentage is at least about 85%. In more preferred embodiments, this percentage is at least about 90%; in other preferred embodiments, this percentage is at least about 95%, 96%, 97%, 98% or 99%. One skilled in the art will understand that the recited ranges include all whole and rational numbers of the range (e.g., 92% or 92.377%).

Helper oligonucleotide. A "helper oligonucleotide" or "helper" refers to an oligonucleotide designed to bind to a target nucleic acid and impose a different secondary and/or tertiary structure on the target to increase the rate and extent of hybridization of a detection probe or other oligonucleotide with the targeted nucleic acid, as described, for example, in U.S. Pat. No. 5,030,557. Helpers may also be used to assist with the hybridization to target nucleic acid sequences and function of primer, target capture and other oligonucleotides. Helper oligonucleotides may be used in the methods described herein and may form part of the compositions and kits described herein.

Blocking moiety. As used herein, a "blocking moiety" is a substance used to "block" the 3'-terminus of an oligonucleotide or other nucleic acid so that it cannot be efficiently extended by a nucleic acid polymerase.

Amplification oligomer. An "amplification oligomer", which may also be called an "amplification oligonucleotide" is an oligomer, at least the 3'-end of which is complementary to a target nucleic acid ("target hybridizing sequence"), and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is a "promoter-based amplification oligomer," which comprises a target hybridizing sequence, and a promoter sequence for initiating transcription by an appropriate polymerase. Promoter-based amplification oligomers may or may not be extended by a polymerase in a primer-based extension depending upon whether or not the 3' end of the target hybridizing sequence is modified to prevent primer-based extension (e.g., a 3' blocked end). A promoter-based amplification oligonucleotide comprising a target hybridizing region that is not modified to prevent primer-based extension is referred to as a "promoter-primer." A promoter-based amplification oligonucleotide comprising a target hybridizing region that is modified to prevent primer-based extension is referred to as a "promoter-provider." Size ranges for amplification oligonucleotides include those comprising target hybridizing regions that are about 10 to about 70 nt long—such as about 10 to about 60 nt long, about 10 to about 50 nt long, about 10 to about 40 nt long, about 10 to about 30 nt long or about 10 to about 25 nt long or about 15 to 25 nt long. Preferred sizes of amplification oligomers include those comprising target hybridizing regions that are about 18, 19, 20, 21, 22 or 23 nt long. An amplification oligomer may optionally include modified nucleotides or analogs that are not complementary to target nucleic acid in a strict A:T/U, G:C sense. Such modified nucleotides or analogs are herein considered mismatched to their corresponding target sequence. For some embodiments, the preferred amount of amplification oligomer per reaction is about 10, 15 or 20 pmoles.

Oligomers not intended for primer-based extension by a nucleic acid polymerase may include a blocker group that replaces the 3'OH to prevent the enzyme-mediated extension of the oligomer in an amplification reaction. For example, blocked amplification oligomers and/or detection probes present during amplification may not have functional 3'OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

Promoter. This refers to a specific nucleic acid sequence that is recognized by a DNA-dependent RNA polymerase ("transcriptase") as a signal to bind to the nucleic acid and begin the transcription of RNA at a specific site.

Promoter-provider. As used herein, a "promoter-provider" or "provider" refers to an oligonucleotide comprising first and second regions, and which is modified to prevent the initiation of DNA synthesis from its 3'-terminus. The "first region" of a promoter-provider oligonucleotide comprises a base sequence which hybridizes to a DNA template, where the hybridizing sequence is situated 3', but not necessarily adjacent to, a promoter region. The target-hybridizing portion of a promoter oligonucleotide is typically at least 10, 11, 12, 13, 14, 15, 16, 17, 18, 19, 20, 21, 22, 23, 24, 25, 30, 35, 40 or 45 nucleotides in length, and may extend up to 50 or more nucleotides in length. The "second region" comprises a promoter sequence for an RNA polymerase. A promoter-provider oligonucleotide is configured so that it is incapable of being extended by an RNA- or DNA-dependent DNA polymerase, (e.g., reverse transcriptase), preferably by comprising a blocking moiety at its 3'-terminus as described above. This modification differentiates promoter providers from promoter primers. Preferably, the promoter portion of a promoter primer or provider is a promoter for a DNA-dependent RNA polymerase from *E. coli* and bacteriophages T7, T3, and SP6, though other promoters or modified version thereof can be used as well.

Terminating oligonucleotide. As used herein, a "terminating oligonucleotide" or "blocker oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand.

Amplification. This refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, eg., produced by using an amplification oligonucleotide that hybridizes to, and initiates polymerization from, an internal position of the target nucleic acid. Known amplification methods include both thermal cycling and isothermal amplification methods. For some embodiment, isothermal amplification methods are preferred. Replicase-mediated amplification, polymerase chain reaction (PCR), ligase chain reaction (LCR), strand-displacement amplification (SDA), and transcription-mediated or transcription-associated amplification are non-limiting examples of nucleic acid amplification methods. Replicase-mediated amplification uses self-replicating RNA molecules, and a replicase such as QB-replicase (eg., U.S. Pat. No. 4,786,600). PCR amplification uses a DNA polymerase, pairs of primers, and thermal cycling to synthesize multiple copies of two complementary strands of dsDNA or from a cDNA (eg., U.S. Pat. Nos. 4,683,195, 4,683,202, and 4,800,159). LCR amplification uses four or more different oligonucleotides to amplify a target and its complementary strand by using multiple cycles of hybridization, ligation, and denaturation (eg., U.S. Pat. Nos. 5,427,930 and 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (eg., U.S. Pat. Nos. 5,422,252; 5,547,861; and 5,648,211). Preferred embodiments use an amplification method suitable for the amplification of RNA target nucleic acids, such as transcription mediated amplification (TMA) or NASBA, but it will be apparent to persons of ordinary skill in the art that oligomers disclosed herein may be readily used as primers in other amplification methods.

Transcription associated amplification. This method of amplification, also referred to herein as "transcription mediated amplification" (TMA) refers to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods are embodiments of amplification methods used for amplifying and detecting HSV target sequences as described herein.

Variations of transcription associated amplification are well known in the art as previously disclosed in detail (eg., U.S. Pat. Nos. 4,868,105; 5,124,246; 5,130,238; 5,399,491; 5,437,990; 5,554,516; and 7,374,885; and PCT Pub. Nos. WO 88/01302; WO 88/10315 and WO 95/03430). The person of ordinary skill in the art will appreciate that the disclosed compositions may be used in amplification methods based on extension of oligomer sequences by a polymerase.

Real-time TMA. As used herein, the term "real-time TMA" refers to single-primer transcription-mediated amplification ("TMA") of target nucleic acid that is monitored by real-time detection means.

Amplicon. This term, which is used interchangeably with "amplification product", refers to the nucleic acid molecule generated during an amplification procedure that is complementary or homologous to a sequence contained within the target sequence. These terms can be used to refer to a single strand amplification product, a double strand amplification product or one of the strands of a double strand amplification product. Double stranded amplicons can, in some aspects, be circularized using adapters. One such adapter is, for example, the SMRTBell (Pacific Biosciences, Menlo Park, Calif.). Circularized double stranded amplicons can be useful for many purposes, including, but not limited to, sequencing reactions.

Probe. A probe, also known as a "detection probe" or "detection oligonucleotide" are terms referring to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence within a larger nucleic acid sequence that hybridizes specifically to at least a portion of a probe oligomer by standard base pairing. A probe may comprise target-specific sequences and other sequences that contribute to the three-dimensional conformation of the probe (eg., U.S. Pat. Nos. 5,118,801; 5,312,728; 6,849,412; 6,835,542; 6,534,274; and 6,361,945; and US Pub. No. 20060068417). In a preferred embodiment, the detection probe comprises a 2' methoxy backbone which can result in a higher signal being obtained.

Stable. By "stable" or "stable for detection" is meant that the temperature of a reaction mixture is at least 2.deg. C. below the melting temperature of a nucleic acid duplex.

Label. As used herein, a "label" refers to a moiety or compound joined directly or indirectly to a probe that is detected or leads to a detectable signal. Direct labelling can occur through bonds or interactions that link the label to the probe, including covalent bonds or non-covalent interactions, e.g. hydrogen bonds, hydrophobic and ionic interactions, or formation of chelates or coordination complexes. Indirect labelling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (e.g., U.S. Pat. Nos. 5,283,174, 5,656,207, and 5,658,737). Labels include chemiluminescent compounds, e.g., acridinium ester ("AE") compounds that include standard AE and derivatives (e.g., U.S. Pat. Nos. 5,656,207, 5,658,737, and 5,639,604). Synthesis and methods of attaching labels to nucleic acids and detecting labels are well known (e.g., Sambrook et al., *Molecular Cloning, A Laboratory Manual*, 2nd ed. (Cold Spring Harbor Laboratory Press, Cold Spring Harbor, N.Y., 1989), Chapter 10; U.S. Pat. Nos. 5,658,737, 5,656,207, 5,547,842, 5,283,174, and 4,581,333). More than one label, and more than one type of label, may be present on a particular probe, or detection may use a mixture of probes in which each probe is labeled with a compound that produces a detectable signal (e.g., U.S. Pat. Nos. 6,180,340 and 6,350,579).

Molecular torches. As used herein, structures referred to as "molecular torches" are designed to include distinct regions of self-complementarity ("the closing domain") which are connected by a joining region ("the target binding domain") and which hybridize to one another under predetermined hybridization assay conditions. All or part of the nucleotide sequences comprising target closing domains may also function as target binding domains. Thus, target closing sequences can include, target binding sequences, non-target binding sequences, and combinations thereof.

Capture oligonucleotide. As used herein, a "capture oligonucleotide," "target capture oligonucleotide" or "capture probe" refers to a nucleic acid oligomer that specifically hybridizes to a target sequence in a target nucleic acid by standard base pairing and joins to a binding partner on an immobilized probe to capture the target nucleic acid to a support. One example of a capture oligomer includes an oligonucleotide comprising two binding regions: a target hybridizing sequence and an immobilized probe-binding region. A variation of this example, the two regions may be present on two different oligomers joined together by one or more linkers. Another embodiment of a capture oligomer the target hybridizing sequence is a sequence that includes random or non-random poly-GU, poly-GT, or poly U sequences to bind non-specifically to a target nucleic acid and link it to an immobilized probe on a support. (PCT Pub No. WO 2008/016988). The immobilized probe binding region can be a nucleic acid sequence, referred to as a tail. Tails include a substantially homopolymeric tail of about 10 to 40 nucleotides (e.g., $A_{10}$ to $A_{40}$), or of about 14 to 33 nt (e.g., $T_3A_{14}$ to $T_3A_{30}$), that bind to a complementary immobilized sequence attached to the support particle or support matrix. Thus, a non-limiting example of preferred nucleic acid tails can in some embodiments include $T_{0-4}A_{10-36}$ sequences. Another example of a capture oligomer comprises two regions, a target hybridizing sequence and a binding pair member that is not a nucleic acid sequence.

Immobilized oligonucleotide. As used herein, an "immobilized oligonucleotide", "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size±5%), to which an immobilized probe is joined directly (via covalent linkage, chelation, or ionic interaction), or indirectly (via one or more linkers), where the linkage or interaction between the probe and support is stable during hybridization conditions.

Complementary. By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g. G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues that are not complementary by standard A:T/U and G:C pairing, or are modified nucleotides such as abasic residues, modified nucleotides or nucleotide analogs. Sufficiently complementary contiguous sequences typically are at least 80%, or at least 90%, complementary to a sequence to which an oligomer is intended to specifically hybridize (a %-complementarity range includes all whole and rational numbers of the range). Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary.

Preferentially hybridize. By "preferentially hybridize" is meant that under stringent hybridization assay conditions, an oligonucleotide hybridizes to its target sequences, or replicates thereof, to form stable oligonucleotide: target sequence hybrid, while at the same time formation of stable oligonucleotide: non-target sequence hybrid is minimized. For example, a probe oligonucleotide preferentially hybridizes to a target sequence or replicate thereof to a sufficiently greater extent than to a non-target sequence, to enable one having ordinary skill in the art to accurately detect the RNA replicates or complementary DNA (cDNA) of the target sequence formed during the amplification. Appropriate hybridization conditions are well known in the art for probe, amplification, target capture, blocker and other oligonucleotides, may be predicted based on sequence composition, or can be determined by using routine testing methods (e.g., Sambrook et al., *Molecular Cloning, A Laboratory Manual*, 2$^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57).

Nucleic acid hybrid. By "nucleic acid hybrid" or "hybrid" or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

Sample preparation. This refers to any steps or methods that treat a sample for subsequent amplification and/or detection of HSV nucleic acids present in the sample. The target nucleic acid may be a minority component in the sample. Sample preparation may include any known method of isolating or concentrating components, such as viruses or nucleic acids using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically captures a target nucleic acid and separates it from other sample components (eg., as described in U.S. Pat. No. 6,110,678 and PCT Pub. No. WO 2008/016988).

Separating, purifying. These terms mean that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components. Ranges of %-purity include all whole and rational numbers of the range.

DNA-dependent DNA polymerase. As used herein, a "DNA-dependent DNA polymerase" is an enzyme that synthesizes a complementary DNA copy from a DNA template. Examples are DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

DNA-dependent RNA polymerase. As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

RNA-dependent DNA polymerase. As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

Selective RNAse. As used herein, a "selective RNAse" is an enzyme that degrades the RNA portion of an RNA:DNA duplex but not single-stranded RNA, double-stranded RNA or DNA. An exemplary selective RNAse is RNAse H. Enzymes possessing the same or similar activity as RNAse H may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes that selectively degrade RNA target sequences or RNA products of the present invention will be readily apparent to those of ordinary skill in the art.

Specificity. The term "specificity," in the context of an amplification system, is used herein to refer to the characteristic of an amplification system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio).

Sensitivity. The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

Relative fluorescence unit. As used herein, the term "relative fluorescence unit" ("RFU") is an arbitrary unit of measurement of fluorescence intensity. RFU varies with the characteristics of the detection means used for the measurement.

Oligonucleotides for the Amplification and Detection of HSV

Oligonucleotides for amplifying and detecting the HSV target typically comprise at least two amplification oligomers. In one embodiment, a first of said amplification oligomers comprises a target hybridizing sequence 15 to 45 nucleotides in length and is configured to target a sequence in a region of the HSV US8.5 ORF corresponding to either nucleotides 124 to 156 of SEQ ID NO:1 or nucleotides 113 to 144 of SEQ ID NO:2. A second of said amplification oligomers comprises a target hybridizing sequence 15 to 45 nucleotides in length and is configured to target a sequence in a region of the HSV US8.5 ORF corresponding to either nucleotides 205 to 230 of SEQ ID NO:1 or nucleotides 172 to 200 of SEQ ID NO:2.

In one embodiment, a first of said amplification oligomers comprises a target hybridizing sequence 15 to 45 nucleotides in length and is configured to target a sequence in a region of the HSV US8.5 ORF corresponding to nucleotides 124 to 156 of SEQ ID NO:1 and a second of said amplification oligomers comprises a target hybridizing sequence 15 to 45 nucleotides in length and is configured to target a sequence in a region of the HSV US8.5 ORF corresponding to nucleotides 205 to 230 of SEQ ID NO:1

In another embodiment, a first of said amplification oligomers comprises a target hybridizing sequence 15 to 45 nucleotides in length and is configured to target a sequence in a region of the HSV US8.5 ORF corresponding to nucleotides 113 to 144 of SEQ ID NO:2 and a second of said amplification oligomers comprises a target hybridizing sequence 15 to 45 nucleotides in length and is configured to target a sequence in a region of the HSV US8.5 ORF corresponding to nucleotides 172 to 200 of SEQ ID NO:2.

In one embodiment, the first amplification oligomer comprises, consists or consists essentially of a target hybridizing sequence configured to target a sequence in a region corresponding to nucleotides 124 to 143 (eg. SEQ ID NO:7) or nucleotides 136 to 156 (eg. SEQ ID NO:8) of SEQ ID NO:1. In another embodiment, the first amplification oligomer comprises, consists or consists essentially of a target hybridizing sequence configured to target a sequence in a region corresponding to nucleotides 113 to 130 (eg. SEQ ID NO:11) or nucleotides 124 to 144 (eg. SEQ ID NO:12) of SEQ ID NO:2.

In a further embodiment, the second amplification oligomer configured to target a sequence in a region corresponding to nucleotides 208 to 230 of SEQ ID NO:1 comprises, consists or consists essentially of the sequence set forth in SEQ ID NO:10, or corresponds to 205 to 224 of SEQ ID NO:1 comprises, consists or consists essentially of the sequence set forth in SEQ ID NO:22. In another embodiment, the second amplification oligomer comprises, consists or consists essentially of a target hybridizing sequence configured to target a sequence in a region corresponding to nucleotides 172 to 193 (eg. SEQ ID NO:16) or nucleotides 180 to 200 (eg. SEQ ID NO:18) of SEQ ID NO:2.

The second amplification oligomer may further comprise a 5' promoter sequence (eg. a T7 promoter sequence). Accordingly, in one embodiment, the second of said amplification oligomers configured to target a sequence in a region corresponding to nucleotides 208 to 230 of SEQ ID NO:1 and additionally comprising a 5' promoter sequence comprises, consists or consists essentially of the sequence set forth in SEQ ID NO:9. In another embodiment, the second of said amplification oligomers configured to target a sequence in a region corresponding to nucleotides 205 to 224 of SEQ ID NO:1 and additionally comprising a 5' promoter sequence comprises, consists or consists essentially of the sequence set forth in SEQ ID NO:21. In another embodiment, the second of said amplification oligomers comprising, consisting or consisting essentially of a target hybridizing sequence configured to target a sequence in a region corresponding to nucleotides 172 to 193 of SEQ ID NO:2 and additionally comprising a 5' promoter sequence comprises, consists or consists essentially of the sequence set forth in SEQ ID NO:15. In another embodiment, the second of said amplification oligomers comprising, consisting or consisting essentially of a target hybridizing sequence configured to target a sequence in a region corresponding to nucleotides 180 to 200 of SEQ ID NO:2 and additionally comprising a 5' promoter sequence comprises, consists or consists essentially of the sequence set forth in SEQ ID NO:17.

Oligonucleotides for amplifying and detecting the HSV target are also shown in Table 1 and include oligonucleotide sequences selected from the group consisting of SEQ ID Nos 7, 8, 9, 10, 11, 12, 13, 14, 15, 16, 17, 18, 19, 20, 21 and 22 and combinations of two or more thereof. Their preferred function is included for each sequence, and for sequences identified as promoter primers as the preferred function, the sequences include a 5' T7 bacteriophage promoter sequence from which a T7 RNA polymerase can initiate transcription under appropriate conditions. Those skilled in the art will appreciate that another 5' promoter sequence may be substituted for the T7 promoter sequence, which would then function with the appropriate RNA polymerase for the chosen other promoter sequence, to make an equivalent promoter primer oligonucleotide. Oligomers having the same target-specific sequences as the promoter primers but without the promoter sequence are also shown as SEQ ID Nos: 10, 16, 18 and 22 and are capable of functioning as primers in amplification systems that do not use promoter primers. Those skilled in the art will recognize that oligomers identified as having a preferred function in target capture have target-specific portions) and optionally include tail portions (eg. $T_3A_{30}$) which may be deleted or substituted with other sequences or binding moieties.

Although sequences are shown in Table 1 as DNA sequences, the sequences include their corresponding RNA sequences, and their complementary (eg. completely complementary) DNA or RNA sequences, including the reverse complements thereof. Embodiments of oligomers may include one or more modified residues affecting the backbone structure (e.g., 2'-methoxy substituted RNA groups), or one or more LNA monomers, preferably at 5' residues of a primer oligomer, or may include a non-nucleotide linker to attach a label to the oligomer. In a preferred embodiment, oligomers that function as probes for RNA targets may be synthesized with 2'-methoxy substituted RNA groups to promote more stable hybridization between probe and target sequences.

Preferred embodiments of target capture oligomers include a target-specific sequence that binds specifically to the HSV target nucleic acid and a covalently linked "tail" sequence (eg. $T_{0-4}A_{10-36}$) used in capturing the hybridization complex containing the target nucleic acid to an immobilized sequence on a solid support. Capture oligomers may include at least one 2' methoxy linkage. Embodiments of capture oligomers may include the target-specific sequence that binds to HSV nucleic acid attached to another binding moiety, e.g., a biotinylated sequence that binds specifically to immobilized avidin or streptavidin. The tail sequence or binding moiety binds to an immobilized probe (eg., complementary sequence or avidin) to capture the hybridized target and separate it from other sample components by separating the solid support from the mixture.

Primer sequences, including promoter primer sequences, bind specifically to the target nucleic acid or its complementary sequence and may contain additional sequences that are not target-specific, eg., the promoter sequence in a promoter primer. A target-specific sequence, with or without an attached promoter sequence, may serve as an amplification oligomer in a variety of in vitro amplification processes. Embodiments of the HSV assays may use amplification methods that require multiple cycling reaction temperatures, such as PCR (U.S. Pat. Nos. 4,683,195, 4,683,202, and 4,800,159), or may be substantially isothermal as in, for example, transcription associated amplification methods, such as TMA or NASBA (e.g., U.S. Pat. Nos. 5,399,491, 5,480,784, 5,824,518, 5,888,779, 5,786,183, 5,437,990, 5,130,238, 4,868,105, and 5,124,246, and PCT Nos. WO 8801302 and WO 8810315). The HSV assays may use amplification systems that are detected during the amplification process (e.g., real time detection) by including probes that emit distinguishable fluorescent signals when the probe is bound to the intended target sequence made during the amplification process. Probes for real time detection include those referred to as "molecular beacon" or "molecular switch" probes (e.g., U.S. Pat. Nos. 5,118,801 and 5,312,728, Lizardi et al., U.S. Pat. Nos. 5,925,517 and 6,150,097, Tyagi et al., Giesendorf et al., 1998, *Clin. Chem.* 44(3):482-6) and "molecular torch" probes (e.g., U.S. Pat. Nos. 6,835,542 and 6,849,412, Becker et al.). Generally, such probes include a reporter dye attached to one end of the probe oligomer (e.g., FAM™, TET™, JOE™, VIC™) and a quencher compound (e.g., TAMRA™ or non-fluorescent quencher) attached to the other end of the probe oligomer, and signal production depends on whether the two ends with their attached compounds are in close proximity or separated.

The assay to detect HSV in a sample includes the steps of amplifying a target region in the target HSV nucleic acid contained in a sample by using amplification oligomers or primers specific for the intended target region, and detecting the amplified nucleic acid by hybridizing it to a probe sequence. Preferred assays use a transcription-associated amplification reaction and detection is at the end of the amplification reaction. For detection, the amplified nucleic acid may be labeled and bound to an unlabeled probe, but preferred embodiments bind a labeled probe to the amplified nucleic acid. For real-time detection, a labeled probe may be used that is detected in a homogeneous system.

Embodiments of amplification oligomers specific for HSV nucleic acid include the amplification oligomers of SEQ ID NOS:7, 8, 11 and 12 and the target-specific sequences of SEQ ID NOS:10, 16, 18 and 22 which are contained in the promoter primers of SEQ ID NOS:9, 15, 17 and 21, respectively.

Embodiments of amplification oligomers specific for HSV-1 nucleic acid include amplification oligomers of SEQ ID NOS:7 and 8 and the target-specific sequence of SEQ ID NO:10, which is contained in the promoter primer SEQ ID NO:9, and SEQ ID NO:22, which is contained in the promoter primer SEQ ID NO:21.

Embodiments of amplification oligomers specific for HSV-2 nucleic acid include amplification oligomers of SEQ ID NOS:11 and 12 and the target-specific sequences of SEQ ID NOS:16 and 18, which are contained in the promoter primers of SEQ ID NOS:15 and 17, respectively.

The methods for detecting HSV nucleic acid include a detecting step that uses at least one probe that binds specifically to the amplified HSV product (RNA or DNA amplicon, preferably RNA amplicon). Preferably, the probe is labeled and produces a signal detected in a homogeneous system, i.e., without separation of bound probe from unbound probe. Preferred probes are labeled with an acridinium ester (AE) compound from which a chemiluminescent signal is produced and detected in a homogeneous system (substantially as described in detail in U.S. Pat. Nos. 5,283,174, 5,656,744, and 5,658,737). Other examples of probes may be labeled with a fluorescent compound which emits a detectable signal only when the probe is bound to its target, e.g., molecular switch, beacon, or torch probes.

In one embodiment, the detection probe is configured to detect a sequence in a region corresponding to nucleotides 173 to 196 of SEQ ID NO:1. Preferably, the detection probe is configured to target a sequence in a region corresponding to nucleotides 173 to 190 (eg. SEQ ID NO:13) or nucleotides 177 to 196 (eg. SEQ ID NO:14) of SEQ ID NO:1. According to this embodiment, the detection probe specifically hybridises to HSV-1 target nucleic acid and does not specifically hybridise to HSV-2 target nucleic acid.

In a further embodiment, the detection probe is configured to detect a sequence in a region corresponding to nucleotides 148 to 169 of SEQ ID NO:2. Preferably, the detection probe is configured to target a sequence in a region corresponding to nucleotides 148 to 167 (eg. SEQ ID NO:19) of SEQ ID NO:2 or nucleotides 150 to 169 (eg. SEQ ID NO: 20) of SEQ ID NO:2. According to this embodiment, the detection probe specifically hybridises to HSV-2 target nucleic acid and does not specifically hybridise to HSV-1 target nucleic acid.

Preferred probes for specific detection of HSV sequences therefore include oligomers of SEQ ID NOS:13, 14, 19 and 20, preferably labeled (eg. AE-labelled).

Preferred probes for specific detection of HSV-1 sequences therefore include oligomers of SEQ ID NOS:13 and 14, preferably labeled (eg. AE-labelled).

Preferred probes for specific detection of HSV-2 sequences therefore include oligomers of SEQ ID NOS:19 and 20, preferably labeled (eg. AE-labelled).

In one embodiment, probes for the specific detection of HSV-1 sequences are labeled differently to probes for the specific detection of HSV-2 sequences. Thus, the signal that is obtained from the labeled probe will be indicative of the presence of HSV-1 or HSV-2 or a combination thereof in the sample, Assays for detection of HSV nucleic acid may include an internal control (IC) nucleic acid that is amplified and detected by using IC-specific primers and probe in the same reaction mixtures used for HSV nucleic acid amplification and detection. Amplification and detection of the IC-specific sequence demonstrates that assay reagents and conditions were properly used even when no HSV-specific signal is detected for a tested sample (i.e., negative samples). The IC may be used as an internal calibrator for the assay that provides a quantitative result. The IC may be a randomized sequence derived from a naturally occurring source that is not HSV.

One embodiment of the invention relates to a method for specifically detecting a HSV-1 target nucleic acid in a sample comprising the steps of: (a) providing a sample suspected of comprising at least a HSV-1 target nucleic acid; (b) contacting said sample with at least two amplification oligomers, wherein a first of said amplification oligomers comprises a target hybridizing sequence 15 to 45 nucleotides in length and configured to target a sequence in a region of the HSV US8.5 ORF corresponding to nucleotides 124 to 156 of SEQ ID NO:1 and wherein a second of said amplification oligomers comprises a target hybridizing sequence 15 to 45 nucleotides in length and configured to target a sequence in a region of the HSV US8.5 ORF corresponding to nucleotides 208 to 230 of SEQ ID NO:1; and (c) performing a nucleic acid detection reaction that detects said amplification product to determine whether a HSV-1 target nucleic acid is present in said sample. The detection probe that is used in the detection reaction may be a probe that is specific for HSV-1—such as SEQ ID NO:13 or SEQ ID NO:14.

Another embodiment relates to a method for specifically detecting a HSV-2 target nucleic acid in a sample comprising the steps of: (a) providing a sample suspected of comprising at least a HSV-2 target nucleic acid; (b) contacting said sample with at least two amplification oligomers, wherein a first of said amplification oligomers comprises a target hybridizing sequence 15 to 45 nucleotides in length and configured to target a sequence in a region of the HSV US8.5 ORF corresponding to nucleotides 113 to 144 of SEQ ID NO:2 and wherein a second of said amplification oligomers comprises a target hybridizing sequence 15 to 45 nucleotides in length and configured to target a sequence in a region of the HSV US8.5 ORF corresponding to nucleotides 172 to 200 of SEQ ID NO:2; and (c) performing a nucleic acid detection reaction that detects said amplification product to determine whether a HSV-2 target nucleic acid is present in said sample. The detection probe that is used in the detection reaction may be a probe that is specific for HSV-2—such as SEQ ID NO:19 or SEQ ID NO:20.

Another embodiment relates to a method for determining the presence of HSV-1 or HSV-2 target nucleic acid in a sample comprising the steps of: (a) providing a sample suspected of comprising HSV-1 and/or HSV-2 target nucleic acid; (b) contacting said sample with at least two amplification oligomers, wherein a first of said amplification oligomers comprises a target hybridizing sequence 15 to 45 nucleotides in length and configured to target a sequence in a region of the HSV US8.5 ORF corresponding to either nucleotides 124 to 156 of SEQ ID NO:1 or nucleotides 113 to 144 of SEQ ID NO:2 and wherein a second of said amplification oligomers comprises a target hybridizing sequence 15 to 45 nucleotides in length and configured to target a sequence in a region of the HSV US8.5 ORF corresponding to either nucleotides 205 to 230 of SEQ ID NO:1 or nucleotides 172 to 200 of SEQ ID NO:2; and (c) performing a nucleic acid detection reaction that detects said amplification product to determine whether a HSV-1 and/or HSV-2 target nucleic acid is present in said sample. The detection probe that is used in the detection reaction may be a probe that is specific for HSV-1—such as SEQ ID NO:13 or SEQ ID NO:14. The detection probe that is used in the detection reaction may be a probe that is specific for HSV-2—such as SEQ ID NO:19 or SEQ ID NO:20. In one embodiment, the amplification product may be contacted with one or more detection probes that specifically hybridise to HSV-1 nucleic acid. In another embodiment, the amplification product may be contacted with one or more detection probes that specifically hybridise to HSV-2 nucleic acid. In another embodiment, the amplification product may be contacted with two or more detection probes that specifically hybridise to HSV-1 and HSV-2 nucleic acids, wherein the detection probes that specifically hybridise to HSV-1 are labeled with a different label to the detection probes that specifically hybridise to HSV-2. Thus, the signal that is obtained from the labeled probe will be indicative of the presence of HSV-1 or HSV-2 or a combination thereof in the sample.

In one embodiment, the oligonucleotide for amplifying and detecting the HSV target does not comprise a target hybridizing sequence 22 nucleotides in length corresponding to nucleotides 134 to 155 of SEQ ID NO:1.

In one embodiment, the oligonucleotide for amplifying and detecting the HSV target does not consist of the sequence 5'-TTCGTCCGTCTTCTGGTAAGGC-3' as described by Sciortino et al. (2001) *J. Virol.* 75, 17 p 8105-8116.

Combinations of Oligonucleotides for the Amplification and Detection of HSV

Combinations of oligomers and probes that can be used for the amplification and detection of HSV are also disclosed.

(i) One preferred combination of amplification oligomers comprises the target-specific sequence of SEQ ID NO:10, which is contained in the promoter primer of SEQ ID NO:9, in combination with SEQ ID NO:7 or SEQ ID NO:8.

(ii) Another preferred combination of amplification oligomers comprises the target-specific sequence of SEQ ID NO:10, which is contained in the promoter primer of SEQ ID NO:9, in combination with SEQ ID NO:11 or SEQ ID NO:12.

(ii) Another preferred combination of amplification oligomers comprises the target-specific sequence of SEQ ID NO:16, which is contained in the promoter primer of SEQ ID No. 15, in combination with SEQ ID NO:11 or SEQ ID NO:12.

(iv) Another preferred combination of amplification oligomers comprises the target-specific sequences of SEQ ID NO:18, which is contained in the promoter primer of SEQ ID NO:17, in combination with SEQ ID NO:11 or SEQ ID NO:12.

(v) Another preferred combination of amplification oligomers comprises the target-specific sequence of SEQ ID NO:16, which is contained in the promoter primer of SEQ ID No. 15, in combination with SEQ ID NO:7 or SEQ ID NO:8.

(vi) Another preferred combination of amplification oligomers comprises the target-specific sequences of SEQ ID NO:18, which is contained in the promoter primer of SEQ ID NO:17, in combination with SEQ ID NO:7 or SEQ ID NO:8.

(vii) One preferred combination of amplification oligomers comprises the target-specific sequence of SEQ ID NO:22, which is contained in the promoter primer of SEQ ID NO:21, in combination with SEQ ID NO:7 or SEQ ID NO:8.

(viii) Another preferred combination of amplification oligomers comprises the target-specific sequence of SEQ ID NO:22, which is contained in the promoter primer of SEQ ID NO:21, in combination with SEQ ID NO:11 or SEQ ID NO:12.

The combinations of amplification oligomers described above may be used together with one or more detection probes. Accordingly, further combinations of oligonucleotides according to the present invention include each of the combinations (i) to (viii) set forth above together with one or more detection probes, which comprise the sequence set forth in SEQ ID NO:13, 14, 19 or 20. Thus, for example, this combination includes combination (i) together with SEQ ID NO:13, 14, 19 or 20; combination (ii) together with SEQ ID NO:13, 14, 19 or 20; combination (iii) together with SEQ ID NO:13, 14, 19 or 20 and so on.

A preferred combination of oligonucleotides is combination (i) or (ii) together with a detection probe, which comprises the sequence set forth in SEQ ID NO:13 or SEQ ID NO:14. This combination may be particularly useful for detecting HSV-1.

Another preferred combination of oligonucleotides is combination (iii) or (iv) together with a detection probe, which comprises the sequence set forth in SEQ ID NO:19 or SEQ ID NO:20. This combination may be particularly useful for detecting HSV-2.

The combinations of amplification oligomers or the combinations of amplification oligomers and detection probes described above may be also be used in combination with one or more target capture oligomers. Accordingly, further combinations of oligonucleotides according to the present invention include each of the combinations (i) to (viii) set forth above together with a target capture oligomer, which comprises the sequence set forth in SEQ ID NO:3, 4, 5 or 6. Thus, for example, this combination includes combination (i) together with SEQ ID NO:3, 4, 5 or 6; combination (ii) together with SEQ ID NO:3, 4, 5 or 6; combination (iii) together with SEQ ID NO:3, 4, 5 or 6 and so on.

Still further combinations of oligonucleotides according to the present invention include each of the combinations (i) to (viii) set forth above together with a detection probe, which comprises the sequence set forth in SEQ ID NO:13, 14, 19 or 20 and a target capture oligomer, which comprises the sequence set forth in SEQ ID NO:3, 4, 5 or 6. Thus, for example, this combination includes combination (i) together with SEQ ID NO:13, 14, 19 or 20 and together with SEQ ID NO:3, 4, 5 or 6; combination (ii) together with SEQ ID NO:13, 14, 19 or 20 and together with SEQ ID NO:3, 4, 5 or 6; combination (iii) together with SEQ ID NO:13, 14, 19 or 20 and together with SEQ ID NO:3, 4, 5 or 6 and so on.

Sample Preparation

Preparation of samples for amplification and detection of HSV sequences may include methods of separating and/or concentrating viruses contained in a sample from other sample components. Sample preparation may include routine methods of disrupting samples or lysing samples to release intracellular contents, including HSV nucleic acids or genetic sequences comprising the US8.5 ORF. Sample preparation before amplification may include an optional step of target capture to specifically or non-specifically separate the target nucleic acids from other sample components. Nonspecific target capture methods may involve selective precipitation of nucleic acids from a substantially aqueous mixture, adherence of nucleic acids to a support that is washed to remove other sample components, other methods of physically separating nucleic acids from a mixture that contains HSV nucleic acid and other sample components.

In one embodiment, HSV target nucleic acids are selectively separated from other sample components by specifically hybridizing the HSV target nucleic acid to a capture oligomer specific for HSV to form a target sequence:capture probe complex. The complex is separated from sample components by binding the target:capture probe complex to an immobilized probe, and separating the target:capture probe:immobilized probe complex from the sample, as previously described (U.S. Pat. Nos. 6,110,678; 6,280,952; and 6,534,273). Target capture may occur in a solution phase mixture that contains one or more capture oligonucleotides that hybridize specifically to target nucleic acids under hybridizing conditions, usually at a temperature higher than the Tm of the tail sequence:immobilized probe sequence duplex. The target:capture probe complex is captured by adjusting the hybridization conditions so that the capture probe tail hybridizes to the immobilized probe, and the entire complex on the support is then separated from other sample components. The support with the attached immobilized probe:capture probe:target sequence may be washed one or more times to further remove other sample components. Other embodiments link the immobilized probe to a particulate support, such as a paramagnetic bead, so that particles with the attached target:capture probe:immobilized probe complex may be suspended in a washing solution and retrieved from the washing solution, by using magnetic attraction. To limit the number of handling steps, the target nucleic acid may be amplified by simply mixing the target sequence in the complex on the support with amplification oligonucleotides and proceeding with amplification steps.

Capture probes including a $dT_3A_{30}$ tail portion are suitable for hybridization to a complementary immobilized sequence, whereas capture probes without this tail portion can be used in conjunction with another ligand that is a member of a binding pair (eg., biotinylated DNA to bind to immobilized avidin or streptavidin). The complex of the capture probe, its target HSV nucleic acid, and an immobilized binding partner or probe facilitate separation of the HSV nucleic acid from other sample components, and optional washing steps may be used to further purify the captured viral nucleic acid.

Amplification of the HSV Target Region

Amplifying the HSV target region using two or more primers may be accomplished using a variety of known nucleic acid amplification reactions. For example, amplification may be achieved using PCR amplification (U.S. Pat. Nos. 4,683,195, 4,683,202, and 4,800,159, Mullis et al.) to produce multiple DNA strands by using thermocycling reactions that separate dsDNA and primers specific for portions of the separated strands to make additional dsDNA molecules by using a DNA polymerase. Well known variations of the basic PCR method may also be used, e.g., reverse-transcriptase PCR that uses RT to produce a cDNA from an RNA template, and then the DNA is amplified by PCR cycles, or PCR coupled with real-time detection, both of which are sometimes referred to as RT-PCR (e.g., TaqMan One-Step RT-PCR kits, Applied Biosystems, Inc., Foster City, Calif.).

Preferably the amplification step uses a transcription-associated amplification reaction, such as TMA (described in detail in U.S. Pat. Nos. 5,399,491 and 5,554,516). A TMA-based assay produces many RNA transcripts (amplicons) from a single copy of target nucleic acid (eg. RNA), and the amplicons are detected to indicate the presence of the target HSV in the sample. Briefly, in TMA-based assays, a promoter-primer hybridizes specifically to the target sequence and reverse transcriptase (RT) that includes RNaseH activity creates a first strand cDNA by extension from the 3' end of the promoter-primer and digests the template strand. The cDNA is then bound by a second primer and a new strand of DNA is synthesized from the end of the second primer using RT to create a double-stranded DNA (dsDNA) containing a functional promoter sequence. RNA polymerase specific for that promoter binds to the promoter sequence and multiple RNA transcripts are produced, which each can act as a template for additional sequence replication using the same steps used for the initial template. Thus, large amounts of single-stranded amplified product are made using substantially isothermal reaction conditions.

Amplification methods that use TMA amplification may include the following steps. Briefly, a single stranded target nucleic acid—such as RNA—containing the target sequence to be amplified is provided. A first amplification oligomer is brought in contact with that target nucleic acid by hybridizing to the target sequence. The first amplification oligomer may be a primer or a promoter primer. A suitable nucleic acid polymerase then generates a nucleic acid strand amplification product that is complementary to the target nucleic acid target sequence. In the instances where the target nucleic acid is an RNA, the RNA is typically degraded leaving just the newly generated amplification product, which is available for hybridization by a second amplification oligomer. Using a primer as the first amplification oligomer, then the second amplification oligomer is a promoter primer or promoter provider. A suitable nucleic acid polymerase uses the newly generated amplification product to which the promoter-based oligomer is hybridized as a primer to make a complementary strand of the unhybridized promoter sequence. If the second amplification oligomer is a promoter primer, then a complementary copy of the amplification product hybridized by the second amplification oligomer is also generated. The now double stranded promoter sequence of the promoter-based amplification is used by a suitable RNA polymerase to initiate transcription and make RNA transcript amplification products. The first amplification oligomer primer can then hybridize the transcribed amplification products and the steps can repeat. Or, the target nucleic acid is RNA and the first amplification oligomer is a promoter-based amplification oligomer. Here, the promoter based amplification oligomer is a promoter primer. A suitable polymerase makes a first amplification product that is complementary to the RNA target sequence. The RNA target nucleic acid is degraded and a second amplification oligomer is hybridized to the amplification product. A suitable polymerase makes a complement strand, thereby generating a double stranded promoter sequence. Transcription is initiated and RNA is transcribed. The transcribed RNA is complementary to the original target nucleic acid, thus the second amplification oligomer hybridizes again and makes the transcribed RNA double stranded. The RNA is degraded and the remaining DNA strand is hybridized by the first amplification oligomer. The amplification steps can repeat. When the target nucleic acid is DNA the first amplification oligomer is a promoter primer and the second amplification is a primer. Amplification generally proceeds as described above, and as is described in the art. See e.g., U.S. Pat. Nos. 4,868,105; 5,124,246; 5,130,238; 5,399,491; 5,437,990; 5,554,516; and 7,374,885; and PCT Pub. Nos. WO 88/01302; WO 88/10315 and WO 95/03430 describing TMA and other variations of transcription-associated amplification. The amplified products may be detected in real-time during amplification, or at the end of the amplification reaction. Detection may be performed by a number of methods. Probe-based detection methods use an oligonucleotide probe comprising a target hybridizing sequence that binds specifically to a target sequence contained in the amplification products. Detection of a signal resulting from the bound probes indicates the presence of the target nucleic acid in the sample.

Nucleic Acid Detection

Detection of the nucleic acids may be accomplished by a variety of methods. Detection methods may use nucleic acid probes comprising a target hybridizing sequence that is complementary to a portion of the amplified product and detecting the presence of the probe:product complex, or by using a complex of probes that may amplify the detectable signal associated with the amplified products (e.g., U.S. Pat. Nos. 5,424,413; 5,451,503; and 5,849,481). Directly or indirectly labeled probes that specifically associate with the amplified product provide a detectable signal that indicates the presence of the target nucleic acid in the sample. For example, if the target nucleic acid is HSV (eg. HSV-1 or HSV-2) RNA, the amplified product will contain a sequence in or complementary to a HSV target sequence. A probe is configured to bind directly or indirectly to a portion of the amplification product to indicate the presence of HSV in the tested sample, Probes that hybridize to the amplified sequences include hairpin oligonucleotides such as Molecular Torches and linear oligonucleotides that substantially do not form conformations held by intramolecular bonds. Preferably, said probes may include labels. Linear probe embodiments may include a chemiluminescent compound as the label, e.g. a chemiluminescent AE compound attached to the probe sequence via a linker (substantially as described in U.S. Pat. Nos. 5,585,481 and 5,639,604, particularly at column 10, line 6 to column 11, line 3, and in Example 8 therein). Examples of labeling positions are a central region of the probe oligomer and near a region of A:T base pairing, at a 3' or 5' terminus of the oligomer, and at or near a mismatch site with a known sequence that is not the desired target sequence. Hairpin or linear probes may be labeled with any of a variety of different types of interacting labels, where one interacting member is usually attached to the 5' end of the probe and the other interacting member is attached to the 3' end of the probe. Dye labeled probes, including dual labeled probes, single labeled probes, AE labeled probes and the like, are generally known. Dual labeled probes can be labeled at one end with a fluorescent label ("F") that absorbs light of a particular wavelength or range and emits light another emission wavelength or range and at the other end with a quencher ("Q") that dampens, partially or completely, signal emitted from the excited F when Q is in proximity with the fluorophore. Such a probe may be referred to as labeled with a fluorescent/quencher (F/Q) pair. One embodiment of a hairpin probe is a "molecular torch" that detects an amplified product to indicate whether a target sequence is present in the sample after the amplification step. A molecular torch probe comprises a target binding domain and a closing domain, as is described above. These domains allow the molecular torch to exist in open and closed conformations, depending on whether the torch is bound to a target. (See also, U.S. Pat. Nos. 6,849,412; 6,835,542; 6,534,274; and 6,361,945). Another hairpin probe embodiment is a "molecular beacon" which is generally described in Tyagi et al., 1998, Nature Biotechnol. 16:49-53, and in U.S. Pat. Nos. 5,118,801; and 5,312,728. Methods for using such hairpin probes to detect the presence of a target sequence are well known in the art.

One method for detecting HSV sequences may use a transcription associated amplification together with a molecular torch. The molecular torch is added before or during amplification, allowing detection to be carried out without the addition of other reagents. For example, a molecular torch may be designed so that the Tm of the hybridized target binding region and closing region complex is higher than the amplification reaction temperature, thusly designed to prevent the probe from prematurely binding to amplified target sequences. After an interval of amplification, the mixture is heated to open the torch regions and allow the target binding regions to hybridize to a portion of the amplification products. The solution is then cooled to close any probes not bound to amplified products by allowing the probe target binding and closing regions to hybridize, which effectively closes the label/quencher pair. Detection is then performed to generate and detect signals from only the probes that are hybridized to the amplified target sequences. For example, the mixture containing the F/Q labeled hairpin probe is irradiated with the appropriate excitation light and the emission signal is measured. In other embodiments, the hairpin detection probe is designed so that the amplified products hybridize to the target binding region of the probe during amplification, resulting in changing the hairpin to its open conformation during amplification, and the amplification reaction mixture is irradiated at intervals to detect the emitted signal from the open probes in real time during amplification.

Probes for the detection of HSV are disclosed in SEQ ID NOS:13, 14, 19 and 20. Advantageously, these probes can be used to discriminate between HSV-1 and HSV-2 nucleic acids since the configuration of the probes utilises a difference between the nucleic acid sequences from HSV-1 and HSV-2. HSV-2 lacks a 39 nucleotide sequence that is located between nucleotides 161 and 199 of the HSV-1 nucleic acid sequence shown in Table 2 as SEQ ID NO:1. The detection probes for HSV-1 (SEQ ID NOS:13 or 14) specifically hybridise to a sequence in a region of the HSV US8.5 ORF corresponding to nucleotides 173 to 190 or 177 to 196 of SEQ ID NO:1, respectively. Since this sequence is not present in HSV-2, then a detection signal will only be obtained with the HSV-1 probe when HSV-1 nucleic acid has been amplified and is detected. The detection probes for HSV-2 (SEQ ID NOS:19 or 20) specifically hybridise to a sequence in a region of the HSV US8.5 ORF corresponding to nucleotides 148-167 or 150-169 of SEQ ID NO:2, respectively. Since at least a portion of this sequence is not present in HSV-1, then a detection signal will only be obtained with one of these probes when HSV-2 nucleic acid has been amplified and is detected.

In a preferred embodiment, the probes for HSV-1 and HSV-2 are labeled with a separately detectable label—such as a 5' fluorophore.—and so it is possible to determine if the signal obtained is from an HSV-1 or an HSV-2 probe. In a further preferred embodiment, each of the probes for HSV-1 and each of the probes for HSV-2 are each labeled with a separately detectable label.

Exemplary Method for the Amplification and Detection of HSV Nucleic Acid

In general, methods used to demonstrate amplification and detection of HSV nucleic acid by using the compositions described herein involve the following steps. HSV RNA is separated from other sample components by using a method that attaches the target HSV nucleic acid to a solid support that is separated from other sample components. In preferred embodiments, viral RNA is separated from other sample components by using a target-capture system that includes a target-specific capture probe for the HSV viral analyte (e.g., using methods steps described in U.S. Pat. Nos. 6,110,678, 6,280,952 and 6,534,273), or a non-specific method for separation of nucleic acids was used (U.S. Pat. No. 5,234,809). Non-specific separation of viral RNA from other sample components is performed by adhering nucleic acids reversibly to a solid support, followed by washing and elution of the adhered nucleic acids into a substantially aqueous solution (e.g., using a QIAAMP™ Viral RNA Mini kit, Qiagen Inc.). Isolated HSV nucleic acid is amplified for specific target sequences contained in the genome by using TMA amplification, and the amplification products are detected after completion of the amplification reaction. Signal can be detected by using a system that incubates the reactions and detects fluorescence at different wavelengths (eg., using a DNA Engine OPTICON™ 2 system or CHROMO4™ Real-Time PCR Detector, Bio-Rad Laboratories, Inc., Hercules, Calif.).

Real-time TMA-based assays may also be used. These assays are typically performed in reaction mixture that contains the analyte nucleic acid, amplification reagent (eg. APTIMA™ reagent, Gen-Probe Incorporated, San Diego, Calif.), a T7 promoter primer (eg. about 9 pmol/reaction), a second primer without a promoter (eg. about 15 pmol/reaction), and a detection probe (eg. about 0.2-0.3 pmol/reaction) for amplicon detection, in a 40 .micro.l reaction (in a well of a standard 96-well plate, covered with a layer of inert oil or sealing device to prevent evaporation). The mixture of target nucleic acid, primers, and probe may be incubated at about 60.deg. C. for about 10 min, cooled to about 42.deg. C. for about 5 min, and then enzyme reagent containing RT and T7 RNA polymerase is added, the mixture is mixed (e.g., 30 sec vortex) and then incubated at about 42.deg. C. for about 75-100 min for isothermal amplification during which detection of fluorescence is performed either during the reaction (eg. every 3 seconds) or at the end of the reaction. Amplification and detection steps may be performed using an incubation and open channel fluorimeter (eg. CHROMO4™, Bio-Rad Laboratories, Inc.) for real-time two-color fluorescence detection. The assays may include an IC, as described above, i.e., a reaction mixture included primers and probe for the target HSV nucleic acid and IC-specific primers and probe, each probe labeled with a separately detectable 5' fluorophore. Real-time fluorescence signals are analyzed and a detection signal (time of emergence) is calculated. Time of emergence is calculated, e.g., by using a method that analyzes the detected signals (relative fluorescence units or RFU) relative to the signal detection times (RFU(t) data points) to determine a time of emergence ("T-time"), which is the time at which a RFU(t) data point reaches a predefined threshold value (described in detail in U.S. application 60/659,874, Scalese et al., filed Mar. 10, 2005; and US published application US2007-0243600). Briefly, RFU(t) data is treated to subtract background signal ("noise" level) and curves (RFU vs time) is normalized to optimize curve fit for data between predetermined minimum and maximum points. In general, samples that contain a higher analyte concentration result in a steeper curve slope and an earlier time of emergence. Average times of emergence are compared to determine the relative efficiencies of the different assay conditions, e.g., to compare for a single known amount of analyte, the time of emergence detected by using a PCR-based assay compared to using a TMA-based assay.

Kits

The oligomers for use in the methods described herein are suited for preparation of kits. Such a kit may comprise containers, each with one or more of the various oligomers optionally together with one or more of the reagents (eg. enzymes) required to perform the methods described herein. The components of the kit may be supplied in concentrated form. A set of instructions for using the components of the kit will also typically be included. Where the kit comprises combinations of oligomers then the individual oligomers may be provided in individual form, with appropriate instructions for mixing same, or combinations thereof that are ready mixed.

Correlation of Detection of a Target Sequence with Diagnosis

The detection of amplified target sequences characteristic of HSV-1 in a biological sample from an individual is indicative of infection by HSV-1. Detection of amplified target sequences characteristic of HSV-2 in a biological sample from an individual is indicative of infection by HSV-2. Detection of both targets in the same sample is indicative of infection by both HSV-1 and HSV-2.

EXAMPLES

Example 1: Reagents for TMA-Based Assays

Unless otherwise specified, reagents commonly used in the TMA-based assays described herein include the following. Sample transport reagent: 110 mM lithium lauryl sulfate (LLS), 15 mM $NaH_2PO_4$, 15 mM $Na_2HPO_4$, 1 mM EDTA, 1 mM EGTA, pH 6.7. Lysis buffer: 790 mM HEPES, 230 mM succinic acid, 10% (w/v) LLS, and 680 mM LiOH monohydrate. Target Capture Reagent (TCR): 250 mM HEPES, 1.88 M LiCl, 310 mM LiOH, 100 mM EDTA, pH 6.4, and 250 .micro.g/ml of paramagnetic particles (0.7-1.05 micron particles, Sera-Mag™ MG-CM) with $(dT)_{14}$ oligomers covalently bound thereto. Wash Solution: 10 mM HEPES, 150 mM NaCl, 6.5 mM NaOH, 1 mM EDTA, 0.3% (v/v) ethanol, 0.02% (w/v) methylparaben, 0.01% (w/v) propylparaben, and 0.1% (w/v) sodium lauryl sulfate, pH 7.5. Amplification reagent: a concentrated solution containing 125 mM HEPES, 26.7 mM rATP, 33.3 mM rGTP, 5 mM each of rCTP and UTP, 1.33 mM each of dATP, dCTP, dGTP and dTTP, 8% (w/v) trehalose, pH 7.7, to which primers and probes may be added. TMA Enzymes: per reaction about 90 U/.micro.l of MMLV reverse transcriptase (RT) and about 20 U/.micro.l of T7 RNA polymerase per reaction (where 1 U of RT incorporates 1 nmol of dTTP in 10 min at 37.deg. C. using 200-400 .micro.M oligo-dT-primed polyA-template, and 1 U of T7 RNA polymerase incorporates 1 nmol of ATP into RNA in 1 hr at 37.deg. C. using a T7 promoter in DNA template). Probe Reagent for AE-labeled probes: a solution of (a) 100 mM Li-succinate, 3% (w/v) LLS, 10 mM mercaptoethanesulfonate (MES), and 3% (w/v) polyvinylpyrrolidon, or (b) 100 mM Li-succinate, 0.1% (w/v) LLS, and 10 mM MES. Hybridization Reagent: (C-type) 100 mM succinic acid, 2% (w/v) LLS, 100 mM LiOH, 15 mM aldrithiol-2, 1.2 M LiCl, 20 mM EDTA, and 3.0% (v/v) ethanol, pH 4.7. Selection Reagent: 600 mM boric acid, 182.5 mM NaOH, 1% (v/v) octoxynol (TRITON® X-100), pH 8.5 to 9.2, to hydrolyze AE labels on unbound oligomers. Detection Reagents for AE labels are Detect Reagent I: 1 mM nitric acid and 32 mM $H_2O_2$, and Detect Reagent II: 1.5 M NaOH (see U.S. Pat. Nos. 5,283,174, 5,656,744, and 5,658,737).

Example 2: Comparison of Different Oligonucleotide Combinations for the Amplification and Detection of HSV-1

This example demonstrates a comparison of different oligonucleotide combinations for the amplification and detection of HSV-1. The different combinations of amplification oligomers and detection probes tested in this experiment are shown in Table 3.

TABLE 3

Different combinations of amplification oligomers and detection probes tested in Example 2.

| Condition | Primer | Promoter primer | Detection probe |
| --- | --- | --- | --- |
| 1 | SEQ ID NO: 9 | SEQ ID NO: 7 | SEQ ID NO: 14 |
| 2 | SEQ ID NO: 9 | SEQ ID NO: 7 | SEQ ID NO: 13 |
| 3 | SEQ ID NO: 9 | SEQ ID NO: 8 | SEQ ID NO: 14 |
| 4 | SEQ ID NO: 9 | SEQ ID NO: 8 | SEQ ID NO: 13 |

The assays used forward primers (9 pmol/reaction), reverse promoter primers (15 pmol/reaction) and a chemiluminescent acridinium ester labeled detection probe (0.32 pmol/reaction) in a TMA reaction performed substantially as described above using a HSV-1 US8.5 in vitro transcribed RNA at an amount equivalent to $10.sup.6$ copies per reaction. Three replicates of each reaction were performed on 2 different days in wells of a standard 96-well plate, using 30 .micro.l of amplification reagent containing the appropriate target oligonucleotides, incubated at 60.deg. C. for 10 min and at 42.deg. C. for 5 min, and then TMA enzymes were added to each reaction in enzyme reagent (10 .micro.l per reaction), reaction were mixed (30 sec vortex), followed by amplification incubation for 45-60 min at 42.deg. C. during which the chemiluminescent probe signal is detected at time intervals. Different temperature conditions were also tested: PostAmp-A (Probe reagent 62.deg. C. for 20 mins, followed by room temperature at 5 mins; Selection reagent 62.deg. C. for 10 mins and ramp down to 23.deg. C. for 5 mins); and PostAmp-B (Probe reagent 60.deg. C. for 15 mins; Selection reagent 60.deg. C. for 10 mins and ramp down to 23.deg. C. for 5 mins). Negative control samples without HSV-1 target nucleic acid provided the background noise signal.

Results of the tests are shown in Tables 4 to 7 and are expressed as RLU for each of the conditions tested.

TABLE 4

Results of experiments testing combinations of amplification oligomers and detection probes in Condition 1.
Condition No. 1

| Day 1 | | | | Day 2 | | | |
|---|---|---|---|---|---|---|---|
| PostAmp-B | | PostAmp-A | | PostAmp-B | | PostAmp-A | |
| HSV (+) | HSV (−) | HSV (+) | HSV (−) | HSV (+) | HSV (−) | HSV (+) | HSV (−) |
| 59,588 | 737 | 89,318 | 703 | 68,473 | 749 | 69,185 | 767 |
| 41,471 | 752 | 39,650 | 826 | 44,762 | 704 | 68,703 | 772 |
| 68,588 | 790 | 99,609 | 712 | 73,172 | 716 | 76,740 | 785 |

TABLE 5

Results of experiments testing combinations of amplification oligomers and detection probes in Condition 2.
Condition No. 2

| Day 1 | | | | Day 2 | | | |
|---|---|---|---|---|---|---|---|
| PostAmp-B | | PostAmp-A | | PostAmp-B | | PostAmp-A | |
| HSV (+) | HSV (−) | HSV (+) | HSV (−) | HSV (+) | HSV (−) | HSV (+) | HSV (−) |
| 524,148 | 4,639 | 677,485 | 1,693 | 362,377 | 3,879 | 596,038 | 2,543 |
| 762,424 | 4,558 | 669,945 | 1,514 | 820,110 | 4,115 | 591,960 | 1,487 |
| 875,136 | 7,140 | 729,304 | 1,739 | 824,273 | 4,111 | 638,320 | 1,455 |

TABLE 6

Results of experiments testing combinations of amplification oligomers and detection probes in Condition 3.
Condition No. 3

| Day 1 | | | | Day 2 | | | |
|---|---|---|---|---|---|---|---|
| PostAmp-B | | PostAmp-A | | PostAmp-B | | PostAmp-A | |
| HSV (+) | HSV (−) | HSV (+) | HSV (−) | HSV (+) | HSV (−) | HSV (+) | HSV (−) |
| 45,004 | 720 | 32,896 | 664 | 35,504 | 670 | 53,547 | 643 |
| 67,960 | 677 | 42,687 | 674 | 27,000 | 664 | 43,767 | 627 |
| 44,790 | 712 | 41,604 | 681 | 31,779 | 698 | 39,110 | 753 |

TABLE 7

Results of experiments testing combinations of amplification oligomers and detection probes in Condition 4.
Condition No. 4

| Day 1 | | | | Day 2 | | | |
|---|---|---|---|---|---|---|---|
| PostAmp-B | | PostAmp-A | | PostAmp-B | | PostAmp-A | |
| HSV (+) | HSV (−) | HSV (+) | HSV (−) | HSV (+) | HSV (−) | HSV (+) | HSV (−) |
| 542,456 | 5,022 | 289,237 | 1,878 | 468,116 | 4,175 | 296,703 | 1,878 |
| 458,538 | 4,720 | 307,878 | 1,193 | 474,033 | 3,923 | 279,755 | 1,193 |
| 519,366 | 4,809 | 268,200 | 1,761 | 476,040 | 3,971 | 252,724 | 1,761 |

The results showed that all of the oligonucleotide combinations tested resulted in the detection of HSV-1. Conditions 2 and 4 resulted in higher signals with condition 2 giving the highest signal.

Example 3: Detection of HSV-1 Target Nucleic Acid in Infected Vero Cell Supernatants and Lysates This example demonstrates the use of oligonucleotide combination 2 from Example 2 in the amplification and detection of HSV-1 in HSV-1 infected Vero cells.

A target capture step using SEQ ID NO:5 was included in this experiment to capture HSV-1 RNA. The assays used forward primers (9 pmol/reaction), reverse promoter primers (15 pmol/reaction) and a chemiluminescent acridinium ester labeled detection probe with a methoxy backbone (0.32 pmol/reaction) in a TMA reaction performed substantially as described above using $10^4$ copies of HSV-1 US8.5 in vitro transcribed RNA, an HSV-1 infected cell supernatant and an HSV-1 infected cell lysate. Four replicates of each reaction were performed in wells of a standard 96-well plate, using 30 .micro.l of amplification reagent containing the appropriate target oligonucleotides, incubated at 60.deg. C. for 10 min and at 42.deg. C. for 5 min, and then TMA enzymes were added to each reaction in enzyme reagent (10 .micro.l per reaction), reaction were mixed (30 sec vortex), followed by amplification incubation for 45-60 min at 42.deg. C. during which the chemiluminescent probe signal is detected at time intervals as described above. PostAmp-B (Probe reagent 60.deg. C. for 15 mins; Selection reagent 60.deg. C. for 10 mins and ramp down to 23.deg. C. for 5 mins) was used. Negative control samples in which HSV-1 US8.5 in vitro transcribed RNA was absent and in which cell supernatants and cell lysates were not infected with HSV-1 provided the background noise signal.

Results of the experiments are shown in Table 8 and are expressed as RLU for each of the conditions tested.

TABLE 8

Detection of HSV-1 target nucleic acid in HSV-1 infected Vero cell supernatants and lysates

| 0 copies of IVT target | $10^4$ copies of IVT target | Uninfected cell supernatant | Uninfected cell lysate | HSV-1 infected cell supernatant | HSV-1 infected cell lystate |
|---|---|---|---|---|---|
| 8,286 | 774,558 | 6,909 | 4,000 | 1,466,856 | 1,574,904 |
| 8,211 | 1,100,028 | 11,117 | 15,515 | 1,504,425 | 1,496,150 |
| 10,214 | 870,792 | 14,022 | 11,220 | 1,517,837 | 1,492,310 |
| 15,482 | 1,029,469 | 16,268 | 11,615 | 1,424,462 | 1,441,754 |

The results show that HSV-1 infected cell supernatants and cell lysates can be detected with low background noise signals.

Example 4: Detection of ATCC Stock of HSV-1 and Determination of Assay Sensitivity This example demonstrates the use of oligonucleotide combination 2 from Example 2 in the amplification and detection of HSV-1 and the sensitivity of detection.

This experiment was carried out essentially as described for Example 3, expect that HSV-1 from the ATCC culture collection was used as the target and the virus was tested in dilutions from 3160 pfu per reaction to 0.948 pfu per reaction. 10 replicates per reaction were also tested.

Results of the experiments are shown in Table 9 and are expressed as RLU for each of the conditions tested. The average result from 10 replicates is shown.

TABLE 9

Detection of ATCC HSV-1 at decreasing pfu per reaction

| 0 copies of IVT target | 10.sup.4 copies of IVT target | 3160 pfu | 948 pfu | 316 pfu | 94.8 pfu | 31.6 pfu | 9.48 pfu | 3.16 pfu | 0.948 pfu |
|---|---|---|---|---|---|---|---|---|---|
| 9,879 | 1,058,631 | 2,411,322 | 1,714,671 | 1,515,375 | 1,336,896 | 881,471 | 299,102 | 92,636 | 37,906 |

The results show that the HSV-1 assay is sensitive for the detection of HSV-1 and is able to detect ATCC HSV-1 at a sensitivity of 1 pfu.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

TABLE 1

Oligomer Sequences for HSV Assays

| SEQ ID | Sequence (5'-3') | Preferred Function |
|---|---|---|
| 3 | atgcgcctcgggcgattgacgtcac<u>ttta</u><br><u>aaaaaaaaaaaaaaaaaaaaaaaaaaa</u> | Target capture |
| 4 | atgcgcctcgggcgattgacgtcac | Target capture |
| 5 | ggtatacagacggagccgttggtg<u>tttaa</u><br><u>aaaaaaaaaaaaaaaaaaaaaaaaaa</u> | Target capture |
| 6 | ggtatacagacggagccgttggtg | Target capture |
| 7 | aggcctccgattcgtccgtc | Primer |
| 8 | cgtccgtcttctggtaaggcg | Primer |
| 9 | <u><u>aatttaatacgactcactatagggaga</u></u>aat<br>tagctcgtctccgacgtccac | Promoter primer |
| 10 | attagctcgtctccgacgtccac | Primer |
| 11 | tcgtcactcccaggcctc | Primer |
| 12 | aggcctcctatccgtccgtcc | Primer |
| 13 | cacgtcggtcgccgaact | Detection probe |
| 14 | tcggtcgccgaactgggcga | Detection probe |
| 15 | <u><u>aatttaatacgactcactatagggaga</u></u>ca<br>atcagttcatcgccgacgtc | Promoter primer |
| 16 | caatcagttcatcgccgacgtc | Primer |
| 17 | <u><u>aatttaatacgactcactatagggaga</u></u>gc<br>gatggcaatcagttcatcg | Promoter Primer |
| 18 | gcgatggcaatcagttcatcg | Primer |
| 19 | ggtaaggcgtcttccgacga | Detection probe |
| 20 | taaggcgtcttccgacgacg | Detection probe |
| 21 | <u><u>aatttaatacgactcactatagggaga</u></u>tc<br>gtctccgacgtccacctc | Promoter Primer |
| 22 | tcgtctccgacgtccacctc | Primer |

Legend:
Target Capture Oligomers- underlined sequences are the polymeric tails.
Promoter Primer Oligomer- double underlined sequences are the promoter sequences.

TABLE 2

DNA sequences of the US8 gene and
US8.5 ORF from HSV-1 and HSV-2

| SEQ ID NO | Sequence 5' → 3' | NCBI information |
|---|---|---|
| 1 | atggatccggctttgagatcttatcaccaacggctccgtctgtataccc
ccgtagcgatgggcatcaatctcgccgcagctcacaacctttggatcc
ggaaggcccgatcgccgttactcccaggcctccgattcgtccgtcttct
ggtaaggcgccccatcccgaggcccacgtcggtcgccgaactgggcga
ccgccggcgaggtggacgtcggagacgagctaatcgcgatttccgacga
acgcggaccccccgacatgaccgcccgcccctcgccacgtcgaccgcg
ccctcgccacacccgcgaccccgggctacacggccgttgtctccccga
tggccctccaggctgtcgacgcccctccctgtttgtcgcctggctggc
cgctcggtggctccggggggcttccggcctgggggccgtcctgtgtggg
attgcgtggtatgtgacgtcaattgcccgaggcgcataa | GenBank Accession No: X14112.1 GI:1944536 REGION: 142744..143223 DNA sequence of the US8.5 ORF of HSV-1 |
| 2 | atggatccggctttgagatcttatcaccaacggctccgtctgtataccc
ccatagcgaggggcgtaaatctcgccgcccgctcaccaccctttggttcg
ggaagcccgggccgtcgtcactcccaggcctcctatccgtccgtcctct
ggtaaggcgtcttccgacgacgcggacgtggcgatgaactgattgcca
tcgcggacgcacgcggggacccgccagagaccctgcccccggcgcggg
cggcgccgcgcccgcgtgccgcagaccacctcgcggcggctcccccgcg
gcctttcccgtggccctccacgccgtggacgccccctcccaattcgtca
cctggctcgccgtgcgctggctgcggggggcggtgggtctcggggccgt
cctgtgcgggattgcgttttacgtgacgtcaatcgcccgaggcgcataa | GenBank Accession No: NC_001798.1 GI:9629267 REGION: 145329..145769 DNA sequence of the US8.5 ORF of HSV-2 |
| 23 | catttaaggcgttgttgtgttgactttgcctcttctggcggggttggtgc
ggtgctgtttgtttgggctcccattttacccgaagatcggctgctatccc
cgggacatggatcgcggggcggtggtggggtttcttctcggtgtttgtg
ttgtatcgtgcttggcgggaacgcccaaaacgtcctggagacgggtgag
tgtcggcgaggacgtttcgttgcttccagctccggggcctacggggcgc
ggcccgacccagaaactactatgggccgtggaacccctggatgggtgcg
gccccttacacccgtcgtgggtctcgctgatgccccccaagcaggtgcc
cgagacggtcgtggatgcggcgtcatgcgcgctccggtcccgctggcg
atggcgtacgcccccccggcccatctgcgaccgggggtctacgaacgg
acttcgtgtggcaggagcgcgcggccgtggttaaccggagtctggttat
tcacgggtccgagagacggacagcggcctgtataccctgtccgtgggc
gacataaaggaccggctcgccaagtggcctcggtggtcctggtggtgc
aaccggccccagttccgaccccaccccgaccccagccgattacgacga
ggatgacaatgacgagggcgaggacgaaagtctcgccggcactcccgcc
agcgggaccccccggctcccgcctcccccgcccccccgaggtcttggc
ccagcgcccccgaagtctcacatgtgcgtggggtgaccgtgcgtatgga
gactccggaagctatcctgttttccccggggagacgttcagcacgaac
gtctccatccatgccatcgcccacgacgaccagacctactccatggacg
tcgtctggttgaggttcgacgtgccgacctcgtgtgccgagatgcgaat
atacgaatcgtgtctgtatcacccgcagctcccagaatgtctgtccccg
gccgacgcgccgtgcgccgcgagtacgtggacgtctcgcctggccgtcc
gcagctacgcggggtgttccagaacaaaccccccaccgcgctgttcggc
cgaggctcacatgagcccgtcccggggctggcgtggcaggcggcctcc
gtcaatctggagttccggacgcgtccccacaacactccggcctgtatc
tgtgtgtggtgtacgtcaacgaccatattcacgcctggggccacattac
catcagcaccgcggcgcagtaccggaacgcggtggtggaacagccctc
ccacagcgcggcgcggatttggccgagcccaccccaccgcacgtcgggg
cccctcccacgcgccccaacccacgcgcgcctgcggttagggcggt
gatgggggccgccctgctgctgtctgcactggggttgtcggtgtgggcg
tgtatgacctgttggcgcaggcgtgcctggcgggcggttaaaagcaggg
cctcgggtaaggggcccacgtacattcgcgtggccgacagcgagctgta
cgcggactggagctcggacagcgagggagaacgcgaccaggtcccgtgg
ctgccccccggagagaccgactctccctccaccaatggatccggct
ttgagatcttatcaccaacggctccgtctgtataccccgtagcgatgg
gcatcaatctcgccgcagctcacaacctttggatccggaaggcccgat
cgccgttactcccaggcctccgattcgtccgtcttctggtaaggcccga
catcccgaggcccacgtcggtcgccgaactgggcgaccgccggcgagg
tggacgtcggagacgagctaatcgcgatttccgacgaacgcggaccccc
ccgacatgaccgcccgcccctcgccacgtcgaccgcgccctcgccacac
ccgcgaccccgggctacacggccgttgtctccccgatggccctccagg
ctgtcgacgcccctccctgtttgtcgcctggctggccgctcggtggct
ccggggggcttccggcctgggggccgtcctgtgtgggattgcgtggtat
gtgacgtcaattgcccgaggcgcataaagggccggtggtccgcctagcc
gcagcaaattaaaaatcgtgagtcacagcgaccgcaacttcccaccccgg
agctttcttccggcctcgatgacgtcccggctctccgatcccaactcct
cagcgcgatccgacatgtccgtgccgctttatcccacggcctcgccagt
ttcggtcgaagcctactactcggaaagcgaagacgaggcggccaacgac
ttcctcgtacgcatgggccgccaacagtcggtattaaggcgtcgacgca
gacgcacccgctgcgtcggcatggtgatcgcctgtctcctcgtggccgt
tctgtcgggcggatttggggcgctcctgatgtggctgctccgctaaaag
accgcatcgacacgcgcgtccttcttgtcgtctctcttccccccccatca
ccccgcaatttgcacccagcctttaactacattaaattgggttcgattg
gcaatgt | US8 gene of NC_001806.1 GI:9629378 (HSV-1) Residues 141139 to 143693 |

TABLE 2-continued

DNA sequences of the US8 gene and US8.5 ORF from HSV-1 and HSV-2

| SEQ ID NO | Sequence 5' → 3' | NCBI information |
|---|---|---|
| 24 | atggctcgcggggccgggttggtgttttttgttggagtttgggtcgtat cgtgcctggcggcagcacccagaacgtcctggaaacgggtaacctcggg cgaggacgtggtgttgcttccggcgcccgcggaacgcacccgggcccac aaactactgtgggccgcggaaccccctggatgcctgcggtccccctgcgcc cgtcgtgggtggcgctgtggcccccccgacgggtgctcgagacggtcgt ggatgcggcgtgcatgcgcgccccggaaccgctcgccatagcatacagt cccccgttccccgcgggcgacgagggactgtattcggagttggcgtggc gcgatcgcgtagccgtggtcaacgagagtctggtcatctacggggcccct ggagacggacagcggtctgtacaccctgtccgtggtcggcctaagcgac gaggcgcgccaagtggcgtcggtggttctggtcgtggagcccgccctg tgccgaccccgacccccgacgactacgacgaagaagacgacgcgggcgt gacgaacgcacgccggtcagcgttccccccccaacccccccccgtcgt cccccgtcgccccccgacgcaccctcgtgttatccccgaggtgtccc acgtgcgcggggtaacgtccatatggagaccctggaggccattctgtt tgccccgggggagacgtttgggacgaacgtctccatccacgccattgcc cacgacgacggtccgtacgccatggacgtcgtctggatgcggtttgacg tgccgtcctcgtgcgccgatatgcggatctacgaagcttgtctgtatca cccgcagcttccagagtgtctatctccggccgacgcgccgtgcgccgta agttcctgggcgtaccgcctggcggtccgcagctacgccggctgttcca ggactacgcccccgccgcgatgttttgccgaggctcgcatggaaccggt cccggggttggcgtggctggcctccaccgtcaatctggaattccagcac gcctcccccccagcacgccggcctctacctgtgcgtggtgtacgtggacg atcatatccacgcctggggccacatgaccatcagcaccgcggcgcagta ccggaacgcggtggtggaacagcaccctccccagcgccagcccgagccc gtcgagcccacccgcccgcacgtgagagcccccatcccgcgccctccg cgcgcggcccgctgcgcctcggggcggtgctggggcggccctgttgct ggccgcctcgggctgtccgcgtgggcgtgcatgacctgctggcgcagg cgctcctggcgggcggttaaaagccgggcctcggcgacgggcccactt acattcgcgtggcggacagcgagctgtacgcggactggagttcggacag cgaggggagcgcgacgggtccctgtggcaggacctccggagagaccc gactctccctccacaaatggatccggctttgagatcttatcaccaacgg ctccgtctgtataccccatagcgaggggcgtaaatctcgccgcccgct caccacctttggttcgggaagcccgggccgtcgtcactcccaggcctcc tatccgtccgtcctctggtaaggcgtcttccgacgacgcggacgtcggc gatgaactgattgccatcgcggacgcacgcggggacccgccagagaccc tgccccccggcgcgggcggcgccgcgcccgcgtgccgcagaccaccctcg cggcggctccccgcggcctttccccgtggccctccacgccgtggacgcc ccctcccaattcgtcacctggctcgccgtgcgctggctgcgggggggcgg tgggtctcggggccgtcctgtgcgggattgcgttttacgtgacgtcaat cgcccgaggcgcataaaggtccggcggccaccccgccgcagctcataaa aatcgtgagtcacggcaaccccaccttcgcctccgccctccgccagcgc ccttccgcgtccgcgatgacctcccggcccgccgaccaagactcggtgc gttccagcgcgtcggtgccgctttaccccgcggcctcgcccgtcccggc agaagcctactactcggaaagcgaagacgaggccgccaacgacttcctc gtgcgcatgggccgccagcagtcggtcctaaggcgccgacggcggcga cgcggtgcgtcgggctggttatcgcctgtctcgtcgtggccctcctatc tggagggttcggggcacttttggtgtggctgctccgctaaatgacgcct cgatgtatgcgccttcttcgcccccacccctcgccgcgacccacgtcc gtatgttaattgcaataaa | US8 gene of NC_001798.1 GI:9629267 (HSV-2) Residues 143843 to 146213 |
| 25 | atggatccggctttgagatcttatcaccaacggctccgtctgtataccc ccgtagcgatgggcatcaatctcgccgccagctcacaaccttggatcc ggaaggcccgatcgccgttactcccaggcctccgattcgtccgtcttct ggtaaggcgcccccatcccgaggccccacgtcggtcgccgaactgggcga ccgccggcgaggtggacgtcggagacgagctaatcgcgatttccgacga acgcggaccccccccgacatgaccgcccgccctcgccacgtcgaccgcg ccctcgccacacccgcgaccccggggctacacggccgttgtctcccga tggccctccaggctgtcgacgccccctccctgtttgtcgcctggctggc cgctcggtggctccggggggcttccggcctggggccgtcctgtgtggg attgcgtggtatgtgacgtcaattgcccgaggcgcataaagggccggtg gtccgcctagccgcagcaaattaaaaatcgtgagtcacagcgaccgcaa cttcccacccggagctttcttccggcctcgatgacgtcccggctctccg atcccaactcctcagcgcgatccgacatgtccgtgccgctttatcccac ggcctcgccagtttcggtcgaagcctactactcggaaagcgaagacgag gcggccaacgacttcctcgtacgcatgggccgccaacagtcggtattaa ggcgtcgacgcagacgcaccgctgcgtcggcatggtgatcgcctgtct cctcgtggccgttctgtcgggcggatttggggcgctcctgatgtggctg ctccgctaaaagaccgcatcgacacgcgcgtccttcttgtcgtctctct tcccccccatcaccccgcaatttgcacccagcctttaactacattaaat tgggttcgattggcaatgt | US8.5 (US8A) gene of NC_001806.1 GI:9629378 (HSV-1) Residues 142744 to 143693 |

Sequence Revision History for GenBank Accession Numbers. Accession Number X14112 was first seen at NCBI on Apr. 21, 1993 as X14112.0 GI:59499; with sequence revisions (X14112.1 GI:1944536) first seen on Apr. 18, 1997. Accession NC_001798 was first seen at NCBI on Aug. 1, 2000 as NC_001798.1 GI:9629267. Accession Number Z86099 was first seen at NCBI on Mar. 5, 1997 as Z86099.1 GI:1869820; with sequence revisions (Z86099.2 GI:6572414) first seen on Dec. 13, 1999. Accession Number NC_001806 GI:9629378 was first seen at NCBI on Aug. 1, 2000.

The invention claimed is:

1. An isolated nucleic acid comprising the sequence of SEQ ID Nos: 13, 14, 19, or 20 or the reverse complement thereof, or the RNA equivalent of any of these sequences, and a detectable label.

2. The isolated DNA or RNA sequence according to claim 1, wherein said sequence is the reverse complement of SEQ ID Nos: 13, 14, 19, or 20.

3. The isolated nucleic acid sequence according to claim 1, wherein the sequence is RNA.

4. The isolated nucleic acid sequence according to claim 1, wherein the sequence is double stranded DNA.

5. The isolated nucleic acid sequence of claim 4, wherein one end of a strand of the nucleic acid is joined to one end of another strand of the nucleic acid by an adapter.

6. The isolated nucleic acid sequence of claim 5, wherein each end of a strand is joined to an end of another strand by adapters, thereby forming a circularized double stranded nucleic acid.

7. The isolated nucleic acid sequence of claim 1, wherein the label is AE.

8. A method of detection HSV-1 or HSV-2 RNA within a sample, comprising separating HSV-1 or HSV-2 RNA from other sample components by attachment to a support, amplifying the HSV-1 or HSV-2 RNA by transcription mediated amplification, contacting amplification product resulting from the amplification with a nucleic acid according to claim 1, wherein presence of a detectable signal from the label indicates presence of HSV-1 or HSV-2 RNA within the sample.

9. The method of claim 8, wherein the attachment to the support is performed using a target capture system comprising a target-specific capture probe of HSV-1 or HSV-2.

10. The isolated nucleic acid of claim 1 comprising the sequence of SEQ ID Nos: 13, 14, 19, or 20.

* * * * *